US009588124B2

(12) United States Patent
El-Sayed et al.

(10) Patent No.: US 9,588,124 B2
(45) Date of Patent: Mar. 7, 2017

(54) SHAPE TUNABLE PLASMONIC NANOPARTICLES

(75) Inventors: Mostafa A. El-Sayed, Atlanta, GA (US); Ivan Homer El-Sayed, San Francisco, CA (US)

(73) Assignees: Georgia Tech Research Corporation, Atlanta, GA (US); The Regents of the University of California, Oakland, CA (US)

( * ) Notice: Subject to any disclaimer, the term of this patent is extended or adjusted under 35 U.S.C. 154(b) by 1383 days.

(21) Appl. No.: 11/913,915

(22) PCT Filed: May 11, 2006

(86) PCT No.: PCT/US2006/018177
§ 371 (c)(1),
(2), (4) Date: Aug. 3, 2009

(87) PCT Pub. No.: WO2006/122222
PCT Pub. Date: Nov. 16, 2006

(65) Prior Publication Data
US 2009/0326614 A1    Dec. 31, 2009

Related U.S. Application Data

(60) Provisional application No. 60/679,901, filed on May 11, 2005, provisional application No. 60/719,360, filed on Sep. 22, 2005, provisional application No. 60/792,016, filed on Apr. 16, 2006.

(51) Int. Cl.
| | | |
|---|---|---|
| *G01N 33/58* | (2006.01) | |
| *A61K 41/00* | (2006.01) | |
| *A61K 49/00* | (2006.01) | |
| *B82Y 5/00* | (2011.01) | |

(52) U.S. Cl.
CPC ....... *G01N 33/587* (2013.01); *A61K 41/0052* (2013.01); *A61K 49/0065* (2013.01); *B82Y 5/00* (2013.01); *B22F 2998/00* (2013.01)

(58) Field of Classification Search
None
See application file for complete search history.

(56) References Cited

U.S. PATENT DOCUMENTS

| 6,530,944 B2 | 3/2003 | West |
|---|---|---|
| 2002/0103517 A1 | 8/2002 | West et al. |

FOREIGN PATENT DOCUMENTS

WO    WO 2004/068405    8/2004

OTHER PUBLICATIONS

Everts. Thermal scalpel to target cancer. Expert Rev Med Devices. Mar. 2007;4(2):131-6.*
Liao and Hafner. Gold Nanorod Bioconjugates. Chem. Mater. 2005. 17, p. 4636-4641.*
Fisher. The Power Density of a Surgical Laser Beam: its Meaning and Measurement. Lasers in Sergery and Medicine. 2: 301-315 (1983).*
Adams, "Monoclonal antibody therapy of cancer," *Nature Biotechnology* 23:1147-1157 (2005).
Alivisatos, "The use of nanocrystals in biological detection." *Nat. Biotech.* 22, 47-52(2004).
Bruchez, "Semiconductor nanocrystals as fluorescent biological labels," *Science* 281:2013-2015(1998).
Chan, "Quantum dot bioconjugates for ultrasensitive nonisotopic detection," *Science* 281:2016-2018(1998).
Ekgasit, "Surface plasmon resonance spectroscopy based on evanescent field treatment", *Anal. Chem.*, 76:561-568 (2004).
El-Sayed, "Surface plasmon resonance scattering and absorption of anti-EGFR antibody conjugated gold nanoparticles in cancer diagnostics: Applications in oral cancer", *American Chemical Society*, 5(5):829-834 (2005).
Huang, "Cancer cells assemble and align gold nanorods conjugated to antibodies to produce highly enhanced, sharp, and polarized surface raman spectra: A potential cancer diagnostic marker", *American Chemical Society*, 7(6):1591-1597 (2007).
Kyo, "Evaluation of MafG interaction with. Maf recognition element arrays by surface plasmon resonance imaging technique", *Genes to Cells*, 9:153-164 (2004).
Nicholson, "EGFR and cancer prognosis," *Eur. J. Cancer* 37(Suppl. 4):S9-S15(2001).
Orwin, "Biomechanical and Optical Characteristics of a Corneal Stromal Equivalent", *J. Biomech, Eng.* 125:439-444 (2003).
Paciotti "Colloidal gold: a novel nanoparticle vector for tumor directed drug delivery," *Drug Deliv.* 11(3):169-83(2004).
Rao, "Characterization of biomimetic surfaces formed from cell membranes", *Biophysical Journals*, 73:3066-3077 (1997).
Sokolov et al. "Optical systems for in vivo molecular imaging of cancer," *Technology in Cancer Research & Treatment* 2(6):491-504(2003).
Sun, "Identification of lithium-regulated genes in cultured lymphoblasts of lithium responsive subjects with bipolar disorders", *Neuropsychopharmacology*, 29:799-804 (2004).
Weissleder, "A clearer vision for in vivo imaging," *Nat. Biotechnol.* 19(4):316-7(2001).
West, "Applications of nanotechnology to biotechnology commentary," *J. Cur. Opin. Biotech.* 11:215-217(2002).
Wickline, "Nanotechnology for molecular imaging and targeted therapy," *Circulation* 107:1092-1095(2003).
Yelin, "Third-Harmonic microscopy with a titanium-sapphire laser" Apply. Phys. B: Lasers and Optics 74 (Suppl.):S97-S101(2002).
Yguerabide, "Light-scattering submicroscopic particles as highly fluorescent analogs and their use as tracer labels in clinical and biological applications," *Analy. Biochem.* 262:137-156(1998).
Yguerabide, "Light-scattering submicroscopic particles as highly fluorescent analogs and their use as tracer labels in clinical and biological applications," *Analy. Biochem.* 262:157-176(1998).
Connor, et al., "Gold nanoparticles are taken up by human cells but do not cause acute cytotoxicity", *Small*, 1(3):325-7 (2005).

(Continued)

Primary Examiner — Michelle S Horning
(74) *Attorney, Agent, or Firm* — Pabst Patent Group LLP

(57) ABSTRACT

Noble metal nanoparticles and methods of their use are provided. Certain aspects provided solid noble metal nanoparticles tuned to the near infrared. The disclosed nanoparticles can be used in molecular imaging, diagnosis, and treatment. Methods for imaging cells are also provided.

12 Claims, 17 Drawing Sheets

(56) References Cited

OTHER PUBLICATIONS

El-Sayed, et al., "Selective laser photo-thermal therapy of epithelial carcinoma using anti-EGFR antibody conjugated gold nanoparticles", *Cancer Lett.*, 239(1):129-35 (2006). Epub Sep. 28, 2005.

Hao, et al., "Synthesis and optical properties of anisotropic metal nanoparticles", *J. Fluoresc.*, 14(4):331-41 (2004).

Huang, et al. "Cancer cell imaging and photothermal therapy in the near-infrared region by using gold nanorods", *J. Am. Chem. Soc.*, 128(6):2115-20 (2006).

Jain, et al. "Calculated absorption and scattering properties of gold nanoparticles of different size, shape, and composition: applications in biological imaging and biomedicine", *J. Phys. Chem. B.*, 110(14):7238-48 (2006).

Link, et al., "Laser photothermal melting and fragmentation of gold nanorods: Energy and laser pulse-width dependence", J Phys Chem., 103(9)1165-70 (1999).

* cited by examiner

HOC cancerous cells

HaCaT noncancerous cells

HSC cancerous cells

SHAPE TUNABLE PLASMONIC NANOPARTICLES

CROSS REFERENCE TO RELATED APPLICATION

This application is a filing under 35 U.S.C. §371 of PCT/US2006/018177 filed with the U.S. Receiving Office of the Patent Cooperation Treaty on May 11, 2006, which claims priority to U.S. Provisional Patent Application No. 60/679,901 filed on May 11, 2005, and U.S. Provisional Patent Application No. 60/719,360 filed on Sep. 22, 2005, and U.S. Provisional Patent Application No. 60/792,016 filed on Apr. 16, 2006, and where permissible, all of which are incorporated by reference in their entirety.

STATEMENT REGARDING FEDERALLY SPONSORED RESEARCH OR DEVELOPMENT

Aspects of the invention were funded in part by Grant Number DE-FG02-97ER14799 awarded by the Department of Energy. The U.S. Government has certain rights in the invention.

BACKGROUND

1. Technical Field

Aspects of the disclosure are generally directed to compositions comprising noble metal plasmonic nanoparticles (those that have characteristic strong surface plasmon resonance absorption and scattering shape tunable spectra) and methods of their use, for example, in the detection and treatment or prophylaxis of hyperproliferative conditions such as cancer.

2. Related Art

The increasing availability of nanostructures with highly controlled optical properties in the nanometer size range has created widespread interest in their use in biotechnological systems for diagnostic application and biological imaging. Cellular imaging utilizing microscope techniques provides anatomic details of cells and tissue architecture important for cancer diagnostics and research. Currently used optical probes include chemiluminescent, fluorimetric and colorimetric techniques. Markers attached to antibodies provide specific information about the presence of specific molecules. Quantum dots are widely used and studied for this application due to their unique size dependent fluorescence properties. But the potential human toxicity and cytotoxicity of the semiconductor material is one major problem for its in vivo application. Colloidal gold nanoparticles have become an alternative consideration due to their easy preparation, ready bioconjugation and potential noncytotoxicity. Immuno-gold nanoparticles conjugated to antibodies have provided excellent detection qualities for cellular labeling using electron microscopy.

Nanoparticles have also been used in photodynamic therapy (PDT) for treating cancer in vivo. In deep tissue, light in the near infrared region is used because near infrared light has maximal penetration through tissue due to the low scattering and absorption of intrinsic chromophores in the tissue. PDT for the management of malignant tumors is gaining acceptance in Europe and United States for various malignancies as new generation of photosensitizers becomes available and technological improvement in the delivery of light occurs. Current PDT agents include molecules preferentially taken up by the tumor cells. Light delivered to a tumor site, in the red region (600-700 nm), photochemically produces singlet oxygen that chemically injures the cell. Photodynamic therapy is distinguishable from photothermal therapy. Photothermal therapy uses heat instead of chemicals to treat cancer and other diseases. However, these agents are only relatively selective and risk of severe burns over the patient's entire body when exposed to light persists for 1 to 30 days depending on the agent used. Further, consistent light penetration in a tumor can be problematic indicating the need for even better photosensitizers and delivery sources.

Other thermal therapies for cancer have been widely investigated as a minimally invasive alternative to conventional surgical treatment. These cause necrosis of the cells through lysis and rupture of membranes and release of digestive enzymes; or denaturation of proteins, ribonucleic acids or deoxyribonucleic acids. A variety of heat sources have been employed such as microwaves, ultrasound and high power laser light as in photothermal therapy. They all have a common limitation that the heating is excessive and nonspecific and destroys both the malignant and benign cells.

Nanoshells composed of a dielectric silica core surrounded by a thin gold shell have been used as photothermal agents due to their wavelength selectivity, strong near infrared absorption efficiency and photo-stability. Nanoshells are disclosed in U.S. Pat. No. 6,530,944 The '944 patent discloses that a serious practical limitation to realizing many applications of solid metal nanoparticles is the inability to position the plasmon resonance at technologically important wavelengths, i.e., near infrared wavelengths. The '944 patent her teaches that solid gold nanoparticles of 10 nm in diameter have a plasmon resonance centered at 520 nm, and that this plasmon resonance cannot be controllably shifted by more than approximately 30 nanometers by varying the particle diameter or the specific embedding medium.

Thus, there is need for compositions and methods useful for detecting or treating pathologies such as cancer.

SUMMARY

The oscillations of electrons in conduction band of noble metal nanoparticles induces strong oscillating electric fields on the surface of the nanoparticle related to its size and shape which strongly enhances the absorption and the scattering crossections to different extents. One aspect of the disclosure provides a method and system in which nanoparticles, for example of gold, silver, or a combination thereof, that have surface plasmon absorption (scattering) in the visible or near infrared region of the spectrum, are conjugated to one or more binding moieties for use in molecular imaging or diagnosis. The light scattering colored nanoparticles can be imaged using a simple conventional light microscope especially in the dark field imaging mode. Another aspect provides a method for differentiating cancer or diseased cells from normal cells in dead cells (microscope), in live cells (microscope), or in vivo (endoscope) by comparing the strong surface plasmon scattering properties of the nanoparticles or by comparing the wavelength of the absorption or scattering spectrum of the surface plasmon oscillation of the nanoparticles.

Another aspect provides noble metal nanoparticle compositions in which the absorption maximum of the nanoparticles is shifted from visible to near infrared when the nanoparticle shape changes from a sphere to rods.

Still another aspect provides a method for detecting a target substance in a sample by administering nanoparticles that specifically interact with a substance via a binding moiety; illuminating the nanoparticles with electromagnetic radiation, and analyzing light scattered or absorbed by the nanoparticles. Light scattered or absorbed by nanoparticles interacting with the target substance can be compared to light scattered or absorbed by nanoparticles in controls, for example a sample of healthy, noncancerous cells. A difference in the intensity or wavelength position of the light scattered or absorbed spectrum of nanoparticles given to controls differs compared to light scattered or absorbed spectrum of the nanoparticles administered to a sample is indicative of the presence of the target substance in the sample. In certain aspects, absorption techniques are used in-vitro and scattering techniques are used in vivo as well as in vitro.

Methods for selective photothermal treatment of pathologies using the disclosed noble metal nanoparticles are also provided. Certain methods of treatment are based on the ability of the disclosed nanoparticles to strongly absorb light and quickly converted that light into heat. In one aspect, the heat damages targeted cells, proteins, or other substances to treat or prevent disease such as cancer.

BRIEF DESCRIPTION OF THE DRAWINGS

FIG. 3 shows a distinguishable difference between malignant and healthy cell images and absorption spectra. Either technique can be used for in-vitro diagnosis.

DETAILED DESCRIPTION

Definitions

Figure 1:
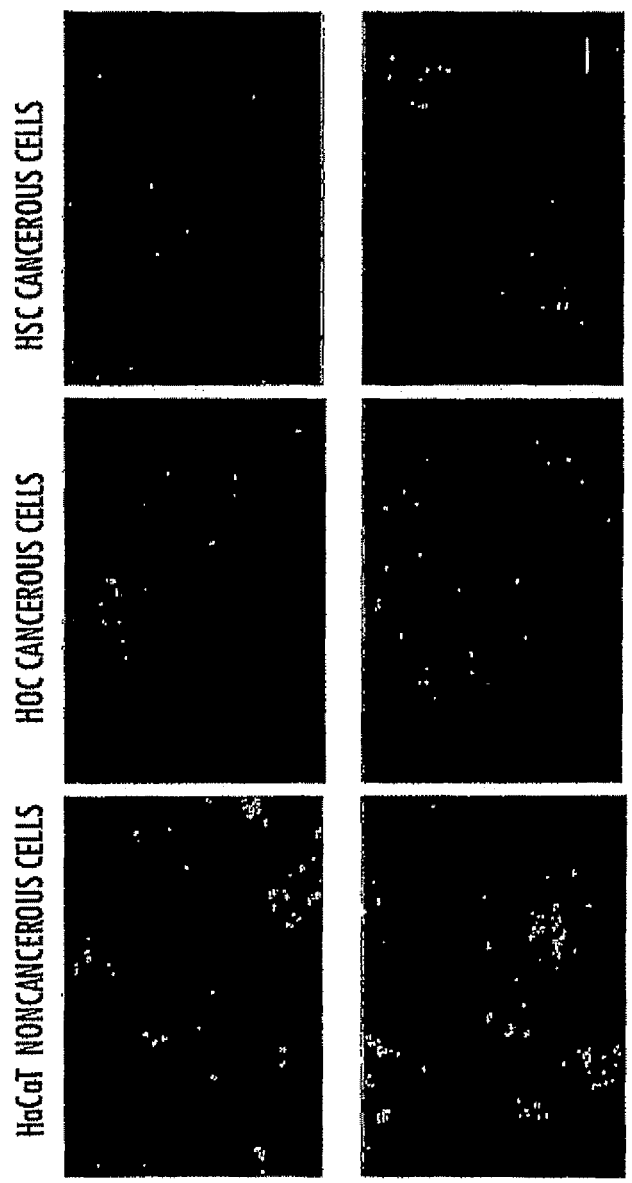
FIG. 1 shows light scattering images of HaCaT noncancerous cells (left column), HOC cancerous cells (middle column) and USC cancerous cells (right column) without gold nanoparticles. Scale bar: 10 μm for all images.
Figure 2A:
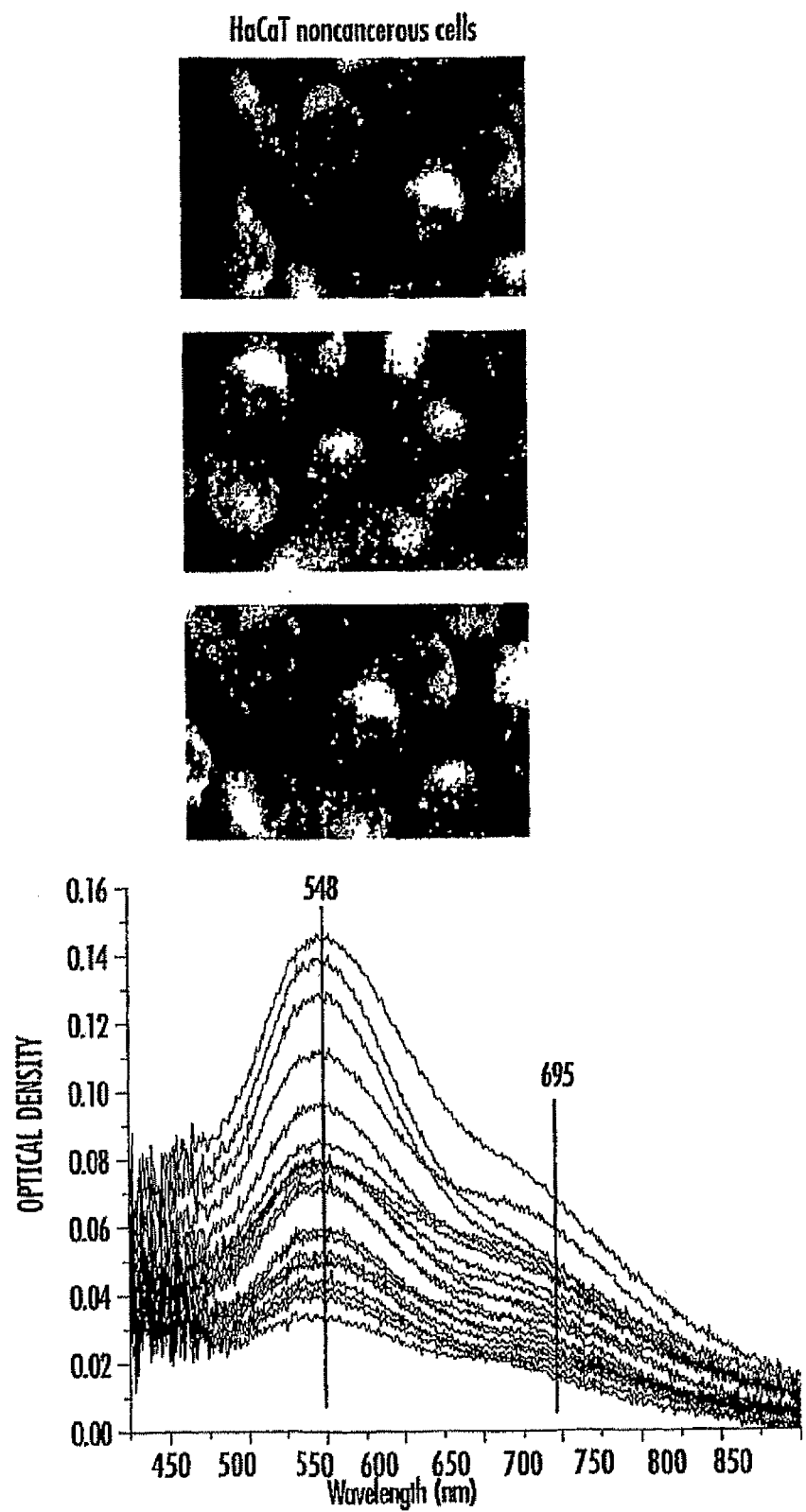
FIG. 2 shows light scattering dark field images and micro-absorption spectra of HaCaT noncancerous cells (left column), HOC cancerous cells (middle column) and USC cancerous cells (right column) after incubation with unconjugated colloidal gold nanoparticles. Scale bar: 10 μm for all images.
Figure 2B:
Figure 2B:
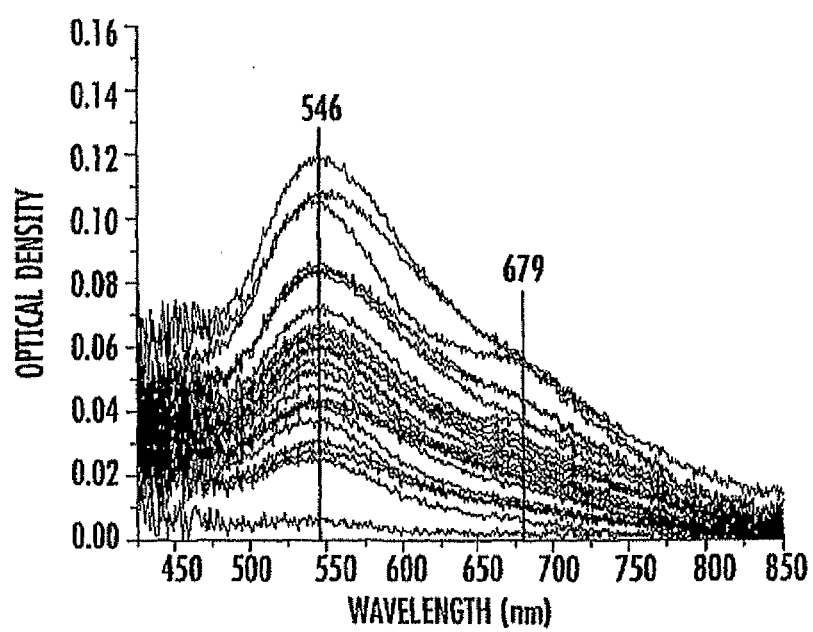
Figure 2C:
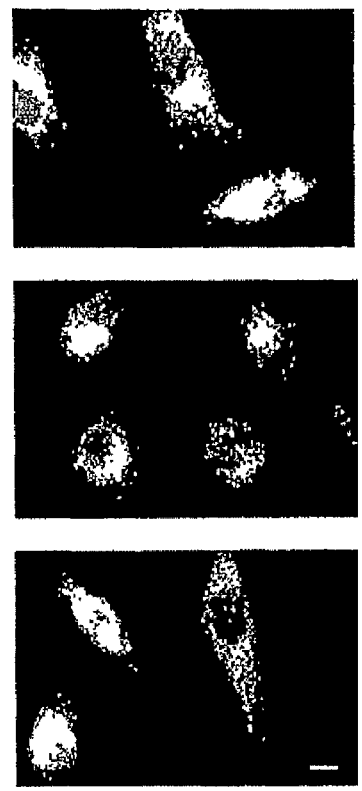
Figure 2C:
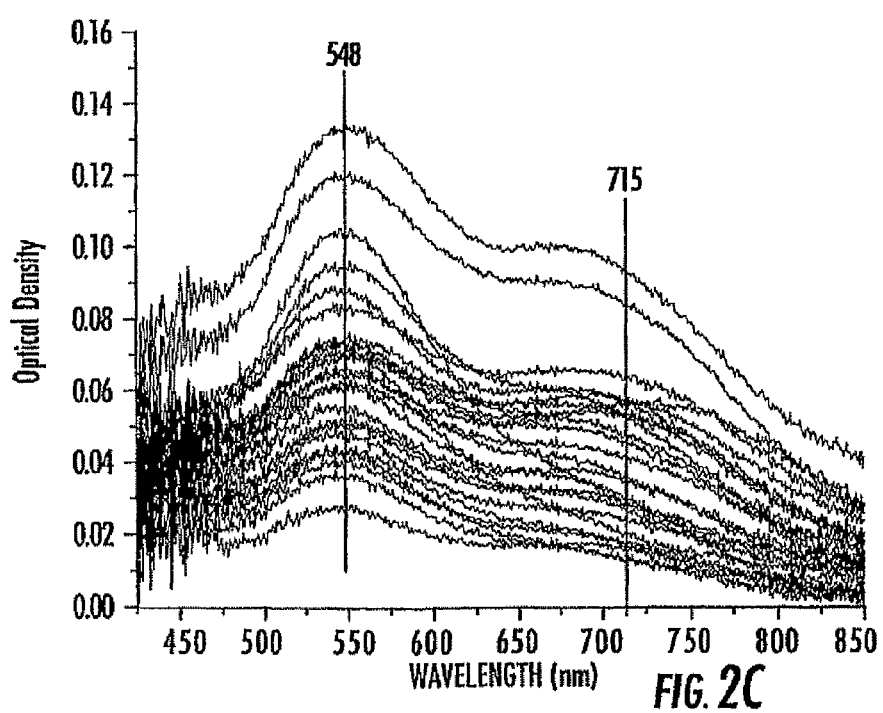

The term "antibody" refers to polyclonal, monoclonal, chimeric, humanized, single chain antibodies or fragments thereof that specifically bind to an antigen. Representative antibody fragments that bind to an antigen include Fab, F(ab')$_2$, and single-chain Fv. Methods for producing antibodies and antibody fragments are known in the art.

The term "aptamer" refers to nucleic acid ligands, for example, short DNA or RNA fragments that can bind to target antigens with high specificity and affinity.

The term "aspect ratio" refers to the length divided by the width of a nanorod.

The term "binding moiety" refers to a substance that specifically binds or interacts with a target substance. Representative binding moieties include, but are not limited to, antibodies, antigen binding antibody fragments, aptamers, ligands, polypeptides, lipids, carbohydrates, biotin/avidin, oligonucleotides, amino acids, deoxyribonucleic acids, ribonucleic acids, small interfering RNA, micro RNA, or other natural or synthetic polymers or binding fragments thereof.

The term "cancer" refers to a variety of malignant neoplasms. Cancer herein is interchangeable with carcinoma, neoplasm, adenocarcinoma, and sarcoma. Medical terminology commonly used for cancer is imprecise with many malignant lesions having names that do not conform to a uniform nomenclature. Cancer in general refers to an abnormal mass or proliferation or tissue or cells, the growth or which is uncoordinated with that of the normal tissue and persists in the same excessive manner after withdrawal of the stimuli which evoked the change.

The term "host" refers to an organism including non-human organisms, primates, mammals, and humans.

The term "nanoparticle" refers to a solid metal particle ranging from about 1 nm to about 1,000 nm in length, width, or diameter. The term includes nanorods, nanospheres, nanocones, nanorectangles, nanopyramids, nanoprisms and other geometric shapes. The disclosed nanoparticles can optionally be coated, for example with a polymer, or conjugated with a binding moiety. Representative nanoparticles include solid noble metal nanoparticles or alloys thereof and are about 1 to about 400 nm in at least one dimension and have surface plasmon absorption (and scattering) in the visible-near infrared region of the spectrum.

The term "noble metal" refers to metals such as gold, silver, or copper.

The term "near infrared" refers to wavelengths of light from about 0.75-1.4 µm.

The term "plasmonic nanoparticles" refers to those nanoparticles that have very strong absorption (and scattering) spectrum that is tunable by changing the shape, the composition or the medium around their surfaces. Plasmonic nanoparticles include but are not limited to nanorods. It will be appreciated that the term includes all plasmonic nanoparticles of various shapes and surface surrounding which gives them surface plasmon absorption and scattering spectrum in the visible-near infra-red region of the spectrum.

The term "pathology" refers to the anatomic or functional manifestations of a disease in an organism. Representative pathologies include, but are not limited to viral, bacterial, fungal, or protist infection, cancer, hyperproliferative conditions such as psoriasis, solid tumors, and hematologic malignancies.

The term "tumor" refers to an abnormal growth of tissue resulting from uncontrolled, progressive multiplication of cells and serving no physiological function. A tumor can be benign or malignant.

1. Nanoparticles

One embodiment of the disclosure provides noble metal nanoparticle compositions for use in the detection, diagnosis, treatment, or prophylaxis of a pathology. The disclosed noble metal nanoparticles, for example gold and silver nanoparticles, absorb strongly in the visible and near-infrared region when the frequency of an electromagnetic field becomes resonant with the surface plasmon coherent electron oscillation within the nanoparticles. Strong absorption spectra is extremely sensitive to the size and aggregation state of the particles. When illuminated with white light at appropriate angles, gold nanoparticles scatter light of many colors. The wavelength distribution of the light in this case is determined by the shape and size of the nanoparticles. The disclosed nanoparticles can be of any geometric shape, including but not limited to spheres, rods, prisms, squares, cones, pyramids, wires, and the like. Gold nanoprisms scatter red, and gold nanorods of aspect ratio of 3.00 scatter orange light. The disclosed nanoparticles can be used as contrast agents for biological and biomedical imaging and sensing using confocal scanning optical microscopy, multiphoton plasmon resonance microscopy, optical coherence microscopy and third-harmonic microscopy.

Certain embodiments provide noble metal nanoparticles conjugated to one or more a binding moieties. The one more binding moieties can be specific for the same or different target substances. It will be appreciated that one binding moiety can have more than one nanoparticle. Methods for conjugating substances to nanoparticles are known in the art and include conjugation via electrostatic charges or covalent bonding. See for example, Sokolov et al. *Technology in Cancer Research & Treatment* 2003, 2(6), 491-504, which where permissible is incorporated by reference in its entirety. Representative binding moieties include, but are not limited to an antibody, antigen-binding antibody fragment, polypeptide, oligonucleotide, aptamer, lipid, or carbohydrate. Generally, the binding moiety specifically binds to a target substance, for example a polypeptide. Most tumors overexpress some type of protein or receptor on the cell surface or in the cytoplasm or nucleus. These overexpressed or tumor specific proteins or receptors can be targeted with a wide variety binding moieties (Gregory P Adams & Louis M Weiner. Nature Biotechnology 23, 1147-1157 (2005)). Representative antibodies or antigen-binding antibody fragments that can be conjugated to the disclosed noble metal nanoparticles include, but are not limited to anti-EGFR, anti-HER2, anti-VEGF, anti-CD20 and anti-CD 52 antibodies. The antibodies can be monoclonal, polyclonal, chimeric, humanized, single-chain antibodies, or antigen-binding fragments thereof.

The antibody can be selected to direct the particle to a tumor or lesion of choice. In this regard, this technique can be useful for any solid tumor, blood borne, or localized tumor within the body, malignant or benign, which has an identifiable overexpressed polypeptide, for example a receptor, and a corresponding antibody or binding moiety.

Representative target substances that can be bound by the binding moiety conjugated to the nanoparticle include, but are not limited to epidermal growth factor receptor, transferrin receptor, platelet-derived growth factor receptor, ErbB2, CD19, CD20, CD45, CD52, Ep-CAM, alpha ($\alpha$)-fetoprotein, carcinoembryonic antigen peptide-1, caspase-8, CDC27, CDK4, carcino-embryonic antigen, calcium-activated chloride channel-2, cyclophilin B, differentiation antigen melanoma, elongation factor 2, Ephrin type-A receptor 2, 3, Fibroblast growth factor-S, fibronectin, glycoprotein 250, G antigen, N-acetylglucosaminyltransferase V, glycoprotein 100 kD, helicase antigen, human epidermal receptor-2/neurological, heat shock protein 70-2 mutated, human signet ring tumor-2, human telomerase reverse transcriptase, intestinal carboxyl esterase, interleukin 13 receptor $\alpha$2 chain, $\beta$-D-galactosidase 2-$\alpha$-L-facosyltransferase, melanoma antigen, melanoma antigen recognized by T cells-1/Melanoma antigen A, melanocortin 1 receptor, macrophage colony-stimulating factor, mucin 1, 2, melanoma ubiquitous mutated 1, 2, 3, New York-esophageous 1, ocular albinism type 1 protein, O-linked N-acetylglucosamine transferase gene protein 15, promyelocytic leukemia/retinoic acid receptor $\alpha$, prostate-specific antigen, prostate-specific membrane antigen, receptor-type protein-tyrosinephosphatase kappa, renal antigen, renal ubiquitous 1, 2, sarcoma antigen, squamous antigen rejecting tumor 1, 2, 3, synovial sarcoma, Survivin-2B, synaptotagmin I/synovial sarcoma, X fusion protein, translocation Ets-family leukemia/acute myeloid leukemia 1, transforming growth factor $\beta$ receptor 2, triosephosphate isomerase, taxol resistant associated protein 3, testin-related gene, tyrosinase related protein 1, tyrosinase related protein 2, folate, ferritin or a fragment thereof. Other potential targets of noble metal nanoparticles include any extracellular or intracellular protein, intracellular organelle, any metabolic target based on preferential uptake by cancer cells, or targets using small interfering ribonucleic acids or deoxyribonucleic acid, or ribonucleic acid.

The target of the binding moiety may be overexpressed on a tumor specifically, such as epithelial growth factor, or targets may be located on adjacent structures such as the vasculature endothelium or extracellular matrix. Developing blood vessels of tumors have different receptors than blood vessels in healthy tumors and represent a target to selectively differentiate tumors from healthy tissue. Blood vessels of many tumors overexpress one or more angiogenesis factors. Overexpressed proteins on the blood vessels supplying the tumor such as vascular endothelium growth factor VEGF) represent a target of monoclonal antibody conjugated noble metal nanoparticle photothermal therapy using anti-VEGF antibody or other specifically directed antibody.

Another embodiment provides noble metal nanoparticles that are optionally coated with a material, for example a polymer, that inhibits or reduces aggregation of the noble metal nanoparticles. Representative coating material includes, but is not limited to CTAB and polyethylene glycol. It will be appreciated that other natural or synthetic polymers can be used as a coating material provided the coating material does not interfere with the optical properties of the noble metal nanoparticles.

Another embodiment provides for delivery of nanoparticles to a tumor or lesion in a carrying vehicle such as a liposome or virus. Nanoparticles with or without a binding moiety attached could be encapsulated as a single particle or in groups within a liposome. Liposomes of certain size will accumulate within a tumor and may serve as a deliver vehicle to a tumor bed. Release of the particles by disruption of the liposome or fusion to the cell wall would allow distribution of particles within or around the tumor. Similarly, viral vectors may carry nanoparticles attached to the outer capsid, or potentially within the viral shell.

Still another embodiment provides noble metal nanoparticles conjugated with a binding moiety and a second agent. The second agent can be a marker or label, radioisotope, chemotherapeutic agent, small molecule, catalytic toxins, drugs, cytokines, enzymes, amino acids, ribonucleic acids, deoxynucleic acids, small interfering ribonucleic acids, or anti-sense DNA.

Chemotherapeutic agents are known in the art, and include but are not limited to 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. These agents or drugs are categorized by their mode of activity within a cell, for example, whether and at what stage they affect the cell cycle.

Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, corticosteroid hormones, mitotic inhibitors, and nitrosoureas, hormone agents, miscellaneous agents, and any analog or derivative variant thereof. Further, gold nanoparticles coated with substances that make them inert to the immune system, such as poly ethylene glycol, will pass through the vasculature and accumulate within the many solid tumors. (Paciotti G F Drug Deliv. 2004 May-June; 11(3):169-83).

Yet another embodiment provides noble metal nanoparticles in which the absorption maximum of the nanoparticles is shifted from visible to near infrared when the nanoparticle shape changes from a sphere to other shapes such as rods. Absorption spectra and scattering depends both on the size and shape of the nanoparticles. Representative nanorods whose spectra are in the near infrared include but are not limited to nanorods having an aspect ratio of about 2.7 to about 6. The aspect ratio can be varied so that the nanorod has an absorption maximum in the near infrared, for example about 800 nm.

Yet another embodiment provides a nanoparticle consisting essential of a noble metal coupled to a binding moiety, optionally capped with a non-toxic, non-pyrogenic, stabilizer, and wherein the nanoparticle has an aspect ratio between 2.5 and 6, and has a plasmon resonance absorption maximum greater than about 600 nm, for example in the near infrared, and wherein the plasmon resonance absorption spectra or the scattering spectrum of the nanoparticle changes when the nanoparticle binding moiety specifically interacts with a target substance.

Another embodiment provides an antibody conjugated to a solid noble metal nanorod having an aspect ratio of about 2.7 to about 10, typically about 3 to about 6, or an antigen binding fragment thereof. The solid metal nanorod absorbs light in the near infrared.

2. Methods of Use

Diagnostics

Noble metal nanoparticles have several advantages for diagnostics and cellular imaging compared to other agents. The disclosed nanoparticles can be used to image live or dead cells, in vitro, in situ or in vivo. They scatter light intensely and they are much brighter than chemical fluorophores. They do not photobleach and they can be easily detected in as low as $10^{-16}$ M concentration. The use of the disclosed nanoparticles can be tailored to the absorption maximum of the nanoparticle. For example, nanoparticles having an aspect ratio of about 1 are spheres. Gold nanospheres of a specific diameter have a maximum absorption of about 520 nm, whereas gold nanorods have a tunable maximum absorbance including the near infrared region where tissue is more transparent. As the aspect ratio increases, the maximum absorption wavelength of the nanorod increase. Using a single excitation source of white light, and taking advantage of the tunable extinction maxima of their surface plasmon resonance scattering and absorption allows for multiply colored nanoparticles to be simultaneously imaged and used as an optical reporter of functional activity of attached probes in vitro, in situ, or in vivo. It will be appreciated that the excitation source can vary. For example, multiple single wavelength light sources can used in combination to illuminate the nanoparticles. Alternatively, multiple wavelength light sources can be used with or without filters to control the wavelengths of light used to illuminate the nanoparticles. Should the scattered spectrum suggest that the cells are cancerous or diseased, the same optical arrangement (fiber optics) can be used to introduce laser light (cw or pulsed) of the appropriate energy sufficient to kill the cells. Thus diagnostics (detection) and treatment can be carried out in combination or alternation. In one embodiment, the exposure of the nanoparticles to electromagnetic radiation in an amount effective to generate heat that selectively damages diseased cells or cells expressing a target substance occur within less than 24, 12, 8, 4, 2, or 1 hour or less than about 30 or less than about five minutes.

Nanospheres

Figure 10:
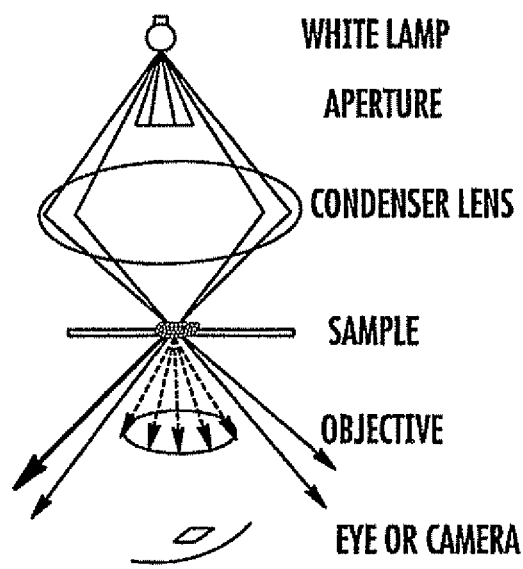
FIG. 10 shows a conventional dark field microscopy configuration.

Accordingly one embodiment provides a method of detecting a target substance on a cell or tissue by contacting a sample with one or more noble metal nanoparticles, for example noble metal nanospheres, conjugated to a binding moiety, wherein the binding moiety is specific for the target substance. Contacting the sample typically occurs in vitro. Surface plasmon resonance scattering imaging or surface plasmon resonance absorption spectroscopy can be used to detect specific binding of the disclosed nanoparticle compositions. The nanospheres can be exposed to electromagnetic radiation, typically white light. It will be appreciated that in certain embodiments the wavelength of light used to expose the nanoparticles is near, includes, or overlaps one or more surface plasmon absorption maxima of the nanosphere or nanoparticle. Light scattering images or absorbance spectra are then detected from the nanospheres in contact with the sample. Under illumination with a beam of white light in dark field microscopy techniques, gold nanospheres of 40 nm to 80 nm diameter scatter strongly green and yellow light respectively. Bright field microscopy or dark field microscopy can be used to obtain images of the sample. Dark field microscopy gives images with better contrast than bright field. A representative dark field microscope configuration is shown in FIG. 10. Cells expressing the target substance on their surface will have nanospheres conjugated around the periphery of the cell, whereas cells that do not express the target substance will represent background signal. Detecting images of cells having nanoparticles specifically bound to a target substance is indicative of the presence of the target substance. Typically, the sample is a biological sample containing a cell, nucleic acid, polypeptide, or other target substance. In one embodiment, the nanospheres are applied directly to the surface of a sample, the surface of a host or patient, or the surface of a biopsy, for example, by spraying, swabbing, wiping, or other noninvasive application method.

Nanospheres conjugated to a binding moiety typically bind homogeneously and specifically to cells expressing a target substance specific for the binding moiety. In certain aspects, cancer cells can express a cancer specific target substance, for example on the exterior or interior of the cell. In such cases, nanospheres conjugated to cancer specific binding moieties will specifically bind to the cancer cell present in a sample and produce a specific and detectable binding pattern that distinguishes cancer cells from noncancerous cells. Certain embodiments of the disclosed gold nanospheres have an absorption maximum at 545 nm when specifically interacting with a target substance, for example on the exterior of a cell. In the presence of cells that do not express the target substance, the gold nanospheres have an absorption maximum of about 552 nm (See FIG. 3). Thus, another embodiment provides a method for detecting a target substance in a sample by contacting the sample with a noble metal nanoparticle, exposing the noble metal nanoparticle to electromagnetic radiation, detecting the absorbance spectra of the nanoparticles of the sample, and comparing the absorbance spectra of the nanoparticles of the sample with the absorbance spectra of unbound nanoparticles, wherein a difference between the absorbance spectra of the nanoparticles of the sample and the absorbance spectra of the unbound nanoparticles is indicative of the presence of the target substance.

Another embodiment provides a method for determining the binding state of a nanoparticle conjugated to a binding moiety. In this method, a nanoparticle conjugated to a binding moiety is contacted with a sample suspected of containing the target substance specifically recognized by the binding moiety. The absorption spectrum of the sample contacted with the nanoparticle is detected and compared with the absorption spectrum of the nanoparticle in the absence of the target substance. A difference between the absorption indicates that the nanoparticle is bound to the target substance in the sample. Gold nanoparticles conjugated to antibodies have a determined absorption and scattering peak. When the antibody binds its target, the absorption and scattering peak shifts. This peak is measurable and determines that the antibody-gold conjugate has bound its target in dead or live whole cells in situ, in vitro and in vivo.

In another embodiment, the amount of a target substance can be quantified on the cell surface based on the plasmon resonance absorption or plasmon resonance scattering of noble metal nanoparticles bound to the target substance. Based on the amount of detectable signal, overexpression of the target substance may be quantified and used as a marker for malignancy.

Still another embodiment provides a method for detecting a target substance by contacting a biologic sample with one or more noble metal nanoparticles conjugated with a binding moiety, for example nanospheres or nanorods, exposing the nanorods with electromagnetic radiation encompassing the plasmon absorbance wavelength of the nanoparticles, detecting the scattering spectrum from the nanoparticles, and comparing the detected scattering spectrum with a control scattering spectrum. A difference between the detected scattering intensity and the control scattering spectral intensity is indicative of the presence of the target substance. If the target substance is a biomarker for cancer or other pathology, the difference in scattering spectra is indicative of cancer or that pathology. Further a red shift in the scattering peak occurs when particles aggregate (when the distance between two particles is less than the distance of the particles' diameter) and particle aggregation may be indicative of cancer or pathology in certain embodiments.

One embodiment provides a method for imaging cells expressing a target polypeptide including the step of contacting one or more cells with a plurality of noble metal nanoparticles. The noble metal nanoparticles are optionally conjugated to a binding moiety specific for the target polypeptide. The nanoparticles are exposed to light which includes the surface resonance scattering wavelength or the surface resonance plasmon absorption maximum of the nanoparticles plus or minus about 50 nm. A bright field or dark field image of the cells is then detected, and an image of the cells is indicative of cells expressing the target polypeptide.

Nanorods

Noble metal nanorods of the appropriate aspect ratio can be effectively used in order to tune the nanoparticle absorption to the near infrared region. Of course, other shapes of noble metal nanoparticles such as prisms and disks can also be used. Gold nanorods provide a contrast reagent for simultaneous molecular imaging and photothermal cancer therapy due to its strong absorption and scattering of visible and near infrared lights. By simply changing the dimensions of the nanorods (the aspect ratio determines the absorption maximum), the strong longitudinal plasmon absorption band can be tuned to various wavelengths, mostly to near infrared region where light penetration through tissue is optimal and minimal tissue damage is expected to occur to the surrounding normal tissues.

The detection of a target substance or the diagnosis of a pathology can be accomplished in vivo using noble metal nanorods having a plasmon resonance absorption maximum tuned in the range of about 675 to 1200 nm, typically about 700 to about 900 nm. This range represents the range of wavelengths that are not substantially absorbed by typical skin (R. Weissleder, Nat, Biotechnol. 2001, 19, 316) or body tissue, Suitable aspect ratios of nanorods are greater than about 2.5, typically about 2.7 to about 10, more typically about 3.8 to about 6. Near infrared light can penetrate about 10 cm in breast tissue, about 4 cm in brain tissue, and about 7 cm in muscle tissue. Visible light penetrates skin to about 5 mm. Ultraviolet light penetrates skin to about 2 mm.

One embodiment provides an in vivo method of detecting a target substance by delivering one or more noble metal nanorods or other shapes of nanoparticles with surface plasmon resonance absorption in the near infrared conjugated to a binding moiety to a site or location suspected of having the target substance, exposing the one or more nanoparticles with near infrared light, for example about 800 nm, detecting the scattering spectrum of the nanoparticles delivered to the site and comparing the detected scattering spectrum with a control spectrum for example the spectrum obtained surrounding cells or tissue, wherein a difference between the detected scattering light spectrum and the control spectrum indicates the presence of a target substance specifically recognized by the binding moiety. A control spectrum can be a spectrum obtained from the surrounding healthy tissue or cells that do not contain the target substance or do not contain detectable levels of the target substance specifically recognized by the binding moiety. In certain embodiments, the nanoparticles, for example nanorods, delivered to the site or location are exposed to electromagnetic radiation encompassing the plasmon resonance scattering wavelength of the nanorods, in particular the longitudinal plasmon resonance wavelength for nanorods. A tunable near infrared laser or other suitable light source can be used to deliver light to the nanoparticles, and a fiber optic light collection system can be used to collect the light scattered by the nanoparticles. The scattered light gives a spectrum characteristic of the nanoparticle surface plasmon scattering spectrum. Locations where nanoparticle surface plasmon scattering spectrum are detected correspond to locations where the target substance is present. The location of the target substance can be indicative of disease such as cancer or viral infection. In certain aspects, the disclosed noble metal nanorods have a longitudinal and a transverse plasmon resonance absorption band. Differences in absorbance or scattering spectra from the transverse plasmon resonance band of nanorods can be used to when the nanorods are exposed to visible light. Thus, the disclosed nanorods can also be used as diagnostic reagents in vitro.

One embodiment provides method for detecting tumor cells by administering a plurality of noble metal nanoparticles to host, wherein the noble metal nanoparticles are coated with a polymer, for example polyethylene glycol in an amount effective to allow the nanoparticles to pass through the vasculature and accumulate in a tumor without the need of a binding moiety. In certain embodiments, the polymer also prevents the excretion of nanoparticles through a kidney of the host by increasing the size of the nanoparticles, if necessary. The nanoparticles are exposed to light including the surface resonance scattering wavelength of the nanoparticles plus or minus about 50 nm. The scattering spectra of the nanoparticles can be detected which is indicative of or correlates with the presence of one or more tumor cells. Concurrent or simultaneous with detection, the nanoparticles can be exposed to an amount of electromagnetic radiation effective to cause the nanoparticles to generate heat which in turn causes damage to one or more tumor cells.

Instrumentation

One embodiment provides a device for simultaneous or concurrent treatment and detection of a pathology. Simultaneous or concurrent means that the detection of the nanoparticles and the exposure of the nanoparticles to electromagnetic radiation in an amount effective to generate heat that selectively damages diseased cells occur within less than 24, 12, 8, 4, 2, or 1 hour or less than about 30 minutes or less than about five minutes. The device includes a means for delivering electromagnetic radiation, for example near infrared light, coupled to a means for detecting light scattered from the disclosed nanoparticles. The device optionally includes a computer or processor. When scattered light is detected at a predetermined intensity by the detecting means, the computer can trigger the means for delivering electromagnetic radiation to deliver an amount of radiation effective to heat the nanoparticles scattering the near infrared light.

Methods of Treatment

The light energy absorbed by noble metal nanoparticles is rapidly converted into heat energy on the picosecond time scale due to rapid electron-phonon and phonon-phonon processes. This generates a temperature rise which is sufficient to cause thermal tissue destruction and cell death thus offering the nanoparticles a novel application in photothermal therapy.

One embodiment provides a method of heating a target by delivering a noble metal nanoparticle to the target, wherein the noble metal nanoparticle is coupled to a binding moiety that specifically interacts with the target, and exposing the nanoparticle to electromagnetic radiation encompassing the plasmon resonance absorption frequency of the nanoparticle. The electromagnetic radiation can be supplied by modest laser irradiation. Representative lasers include, but are not limited to CW argon lasers, CW Ti:Sapphire, as well as pulsed lasers. Electromagnetic radiation absorbed by the nanoparticles is converted to heat. Light can be delivered through fiber optics and the dose can be calculated based on exposure time. This, local selective heating in the vicinity of noble metal nanoparticles can be applied for the thermal destruction of diseased cells, including but not limited to cancer cells or virally infected cells. In certain other aspects, the nanoparticles can be targeted to bacteria, fungus, parasite, or virus that has infected a host. Local selective heating can be used to kill the targeted infectious agent. The heat can be used to denature proteins or other biological polymers at specific locations.

Nanospheres or other nanoparticles whose surface plasmon frequency is in the visible range can be used in vivo for selectively delivering heat to pathologies that are within about 5 mm of an exposed surface. Representative pathologies that can be treated with the disclosed noble metal pathologies, include but are not limited to topical pathologies such as skin cancer, skin infections, cancer of the mouth, throat, or any cancer or pathology in the lining the digestive system. Light of the appropriate wavelength to treat interior pathologies can be delivered using optical fibers, lenses, or combinations thereof.

Typically, the laser density used to expose the noble metal nanospheres is less than about 57 W/cm$^2$, less than about 50 W/cm$^2$, less than about 45 W/cm$^2$, less than about 40 W/cm$^2$, less than about 35 W/cm$^2$, less than about 30 W/cm$^2$. In another embodiment, the laser density need to kill targeted, diseased or cancerous cells is correlated to the number of nanoparticles that specifically interact with the targeted, diseased or cancerous cell. Generally, the binding moiety coupled to the nanoparticle is selected to so that a sufficient number of nanoparticles specifically interact with the target substance, for example on a targeted, diseased or cancerous cell, so that the laser density needed to kill the targeted, diseased, or cancerous cell is less than about 80%, 75%, 70%, 65%, 60%, 55%, 50%, 45%, 40%, 35%, 30%, 25%, or 20% of the laser density required to kill a non-targeted, non-diseased, or noncancerous cell in an environment having nanoparticles that are not specifically bound to the healthy cells.

The disclosed noble metal nanorods or other solid nanoparticles of shapes and configurations that make their surface plasmon resonance absorption in the near infrared region can be used for in vivo diagnostic and treatment of a pathology because the nanorods absorb electromagnetic radiation at near infrared or infrared wavelengths which can penetrate up to about 0.1 to about 10 nm of certain tissues. The absorbed light is rapidly converted into heat. Thus, one embodiment provides a method for treating a pathology in a host by delivering noble metal nanorods or other solid noble metal nanoparticles in vivo to the pathology, wherein the nanorods are coupled to a binding moiety that specifically interacts with the pathology, and exposing the nanorods to near infrared or infrared light. Typically, the pathology is within 10 cm of an exterior surface of the host for direct exposure to near infrared light. The light source can be any suitable light source, for example a near infrared laser. In a particular embodiment, the nanorods have a plasmon resonance absorption spectrum of about 750 to about 900 nm, more typically of about 800 nm. In one embodiment, the plasmon resonance scattering spectra of the nanorods can be detected and compared to control spectra, wherein a difference between the intensity and/or the frequency of the detected spectra and that of the control spectra or that of neighboring normal tissue or cells indicates the presence of the target substance, pathology or disease in the host. The nanorods can then be exposed with infra red or near infrared light in an amount effective to thermally damage the pathology or targeted cells.

One embodiment provides a method for treating a pathology including delivering one or more noble metal nanoparticles coupled to a binding moiety that specifically binds to a target substance expressed by the pathology to a region of a host having or suspected of having the pathology and exposing the one or more noble metal nanoparticles to light with a laser at a laser density of about 50% less than a laser density effective to kill healthy cells unbound by the noble metal nanoparticles. The one or more noble metal nanoparticles absorbs the light and converts the absorbed light to heat.

Another embodiment provides method for detecting a pathology including contacting a host with one or more noble metal nanoparticles conjugated with one or more binding moieties that specifically bind to a polypeptide or nucleic acid associated with the pathology and exposing the one or more noble metal nanoparticles with near infrared light. The method also includes detecting plasmon absorption or plasmon scattering spectra of the one or more nanoparticles. The spectra are compared with control plasmon absorption scattering spectra, and a detectable difference between the detected plasmon absorption or scattering spectra and the respective control spectra is indicative of the pathology.

Selective photothermal therapy is useful for a large number of benign and malignant diseases including solid tumors, blood borne malignancies, and benign lesions. Many malignancies overexpress a cell surface receptor that can be targeted with a monoclonal antibody. Many solid epithelial tumors overexpress epithelial growth factor receptor such as head and neck squamous cell cancer of the oral cavity, larynx, nasopharynx, pharynx, paranasal sinuses. Cancers of skin including squamous cell cancer, basal cell cancer and basosquamous cancer represent targets. Many other cancers of several organs can overexpress epithelial growth factor such as the brain (neuroblastoma, glioma, astrocytoma, malignant mengiomas, etc), cancers of the entire gastrointestinal tract (stomach, duodunem, small bowel, colon, rectum), the respiratory tract (lung, bronchi, trachea), and cancers of the breast, cervix, prostate, vulva, penus, bladder and genitourinary tract. Specific cancers may be squamous cell carcinomas, adenocarcinomas, small cell carcinomas, non small cell carcinomas, neuroendocrine tumors etc.

Other nonepithelial tumors also demonstrate cell surface protein receptors that represents an analogous situation of the EGFR/epithelial cancer models. For instances salivary gland adenocarcinomas overexpress fibroblast growth factor receptor IIIC (FGFR IIIC) and fibroblast growth factor receptor 4 (FGFR4). Soft tissue sarcomas, spindle cell neoplasms, and angiogenic neoplasms. (i.e. angiosarcoma, hemangioma, hemangioendothelioma) and neural derived tumors represent targets with appropriately directed monoclonal antibodies. Tumor profiling of an individuals cancer can be used to determine the best antibody target on an individual basis.

Tumors originating in one organ can spread via lymphatics or blood to other sites such as to lymph nodes or the lung, liver, bone, etc. These metastatic tumors represent potential targets to shrink or decrease tumor size.

Other potential targets include premalignant lesions such as dysplasia, carcinoma in situ, or leukoplakia in epithelial tumors overexpress cell surface receptors, such as epithelial growth factor. Premalignant lesions represent a target of gold nanorod photothermal therapy using monoclonal antibodies, or other bioconjugated molecules.

Nasal polyps overexpress epithelial growth factor. Benign leukoplakia is exposed to cell surface and amenable to topical delivery nanoparticles, Several skin lesions such as actinic keratosis, viral related warts, keratoacanthoma may approached with topical application or direct injection of noble metal nanoparticles.

Several benign lesions located in difficult to reach places, such as the skull base, middle ear, head and neck, lung, abdomen and colon, may be treatable with photothermal therapy in lieu of radiation therapy. Lesions such as schwannomas, benign menigiomas, adenomas (all types), lipomas, benign hemangiomas, etc may be directly injected with gold nanorods or targeted via intravascular delivery and subsequently treated with photothermal therapy. In the case of meningiomas, which can overexpress EGFR, subtotal resection is often undertaken by neurosurgical teams due to proximity to vital structures. In these situations, topical application to residual meningioma and photothermal therapy intraoperatively may be carried out.

Vascular and lymphatic malformations, cystic lesions such as branchial cleft cyst, lymphoepithelial cyst, hemangiomas targeted with antibodies to vascular endothelial growth factor receptors, lipomas may be treated through direct injection of particles into the lesion and exposing the nanoparticles to a sufficient amount of electromagnetic radiation to treat the pathology. In certain aspects, the nanoparticles are not conjugated to a binding moiety.

General Clinical Application of the Use of Plasmonic Nanoparticles and Laser Technologies Silver nanoparticles have very similar properties to gold nanoparticles and thus all the previous discussion and the forthcoming discussion apply very much to silver nanoparticles as they are to gold nanoparticles. For clinical application of treating cancer in vivo under the skin, near infrared lasers are needed as it has larger penetration depth. Light in the region between 650-900 nm has a penetration longer of at least several centimeters depending on the types of tissue. In the present disclosure, the absorption of the nanoparticles is tuned by changing the shape of the solid pure gold or silver nanoparticles. Rods have been tuned to the near infrared region by changing the rod aspect ratio. Other particle shapes also have strong surface plasmon absorption in this region. Since the absorbance/unit area of the cell surface of bound solid gold nanoparticles is much larger than that of the core-shell nanoparticles, lower laser or light energy will be needed to kill the cancer cells selectively by using the solid gold nanoparticles than by using core shell nanoparticles. This makes the use of laser or light treatment less toxic. The use of the laser plasmonic nanoparticle therapy could thus be of more general use. The treatment of cancer in tissue under the skin, solutions of antibody conjugated nanoparticles suitable for the receptors on the cancer being treated are injected in the cancer region. Light can also be delivered by the same needle system or by optical fiber in the form of needle to reach the cancer region. In another treatment, the near IR laser light beam could be focused with a lens located externally and with a focal length that could focus the laser beam where the gold or silver nanoparticles bound to the cancer cells is located under the skin. If the laser light is focused on the nanoparticles of a shape that does not have a center of symmetry and has a surface plasmon absorption in the near infrared, harmonic generation will take place. The near infrared light will double in frequency with enhanced probability due to the presence of the nanoparticles. The higher energy photons at twice the near infrared frequency could be absorbed producing more heat and doing more damage or annealing to the region where the nanoparticles are located.

It will be appreciated that the methods disclosed herein can be used in combination or alternation with other therapeutic methods. For example, if the pathology to be treated is cancer, methods employing the disclosed noble metal nanoparticles can be combined with existing cancer therapies such as radiation therapy or chemotherapy. Anti-inflammatory agents, antioxidants, antibiotics, can also be used in conjunction with the disclosed methods. In one embodiment, the pathology is heated using the disclosed compositions, for example to sensitize the pathology to a second therapeutic or treatment. The heated pathology can then be further treated with a second therapy. Cancer can be sensitized to radiation by preheating of the tissue using the disclosed methods and compositions.

Another embodiment provides a method for determining when a probe is bound to a target. The method includes contacting a sample with the probe, wherein the probe includes a noble metal nanoparticle conjugated to a binding moiety specific for the target. The unbound probe has a specific resonance plasmon absorption maximum. The probe is exposed to electromagnetic radiation, and a second resonance plasmon absorption maximum from the probe contacting the sample is detected. A detectable difference between the first resonance plasmon absorption maximum and the second resonance plasmon absorption spectrum indicates the probe is bound to the target.

3. Methods of Administration

The disclosed nanoparticles may be delivered to a desired cell or location in a cell or tissue using delivery vehicles such as liposomes, viral vectors, dendrimers, or polymeric carriers. Gold nanoparticles can be delivered to tumors after intravascular injecting through mechanisms unrelated to monoclonal antibodies. It is known that gold nanoparticles coated in poly ethylene glycol will be inert to the immune system and pass through poorly formed, leaky blood vessels associated with many tumors. The particles then accumulate in the extracellular matrix around the tumor.

In another embodiment noble metal nanoparticles, for example nanorods, can be injected directly into a lesion, applied topically to epithelial lesions or lesions exposed during surgery, injected intravascularly and transported through the vasculature as individual particles or within transport vehicles such as liposomes or viruses. Liposomes packaged with gold nanorods will accumulate in tumor beds, Liposomes may then conjugate with the cell wall of the tumor and deliver gold nanorods or nanoparticles directly into the tumor cells. Similarly, the facile surface chemistry of gold nanoparticles allows for conjugation of the particles to a variety molecules through thiol linkages.

Alternatively, gold nanoparticles could be ingested for topical delivery to the gastrointestinal tract, or nebulized in a liquid carrier for delivery to the respiratory tract Gold nanoparticles could be used to target the vasculature of the tumor or the extracellular matrix of the tumor without actually entering the tumor cells directly. The nanoparticles can also be topically applied directly with endoscopic technology.

In addition to delivery of fully formed gold nanorods to cells, gold nanoparticles can also be self assembled within living cells by delivery of gold salts to the tumor and allowing the gold ions to be reduced within the cells or extracellular matrix. Transport vectors such as liposomes, viral vectors, or individual molecules could be used to deposit the gold salt into cells which then are reduced and make nanoparticles in the reducing environment of the cell.

Still another embodiment provides noble metal nanoparticles conjugated with a moiety for facilitating translocation of a cell membrane or for targeting the nanoparticle to a specific cell, tissue, intracellular organelle, or interior region of a cell. Translocation moieties include, but are not limited to natural or synthetic polypeptides having a net positive charge. Representative translocation moieties include protein transduction domains (PTD) or cell penetrating peptides (CPT). PTD domains are know in the art and include but are not limited to: 1. TAT protein transduction domain (PTD) KRRQRRR (SEQ ID NO: 1); 2. Penetratin PTD RQIKIWPQNRRMKWKK (SEQ ID NO: 2); 3. VP22 PTD DAATATRGRSAASRPTERPRAPARSASRPRRPVD (SEQ ID NO: 3); 4. Kaposi FGF signal sequences AAVALLPAVLLALLAP (SEQ ID NO: 4), and AAVLLPVLLPVLLAAP (SEQ ID NO: 5); 5. Human β3 integrin signal sequence VTVLALGALAGVGVG (SEQ ID NO: 6); 6. gp41 fusion sequence GALFLGWLGAAGSTMGA (SEQ ID NO: 7); 7. Caiman crocodylus Ig(v) light chain MGLGLHLLVLAAALQGA (SEQ ID NO: 8); 8. hCT-derived peptide LGTYTQDFNKFHTFPQTAIGVGAP (SEQ ID NO: 9); 9. Transportan GWTLNSAGYLLKINLKALAALAKKIL (SEQ ID NO: 10); 10. Loligomer TPPKKKRKVEDPKKKK (SEQ ID NO: 11); 11. Arginine peptide RRRRRRR (SEQ ID NO: 12); and 12. Amphiphilic model peptide KLALKLALKALKAALKLA (SEQ ID NO: 13); and variants or combinations thereof.

The disclosed nanoparticles may be delivered using a non-endocytic uptake pathway or an endocytic uptake pathway. The endocytic route may require a ligand which has both targeting and delivery functions e.g., folic acid for targeting folic acid receptors on cancer cells. The ligand may also be an antibody. In certain other preferred embodiments, the endocytic route targeted delivery may be supplemented with endosomal disruption agents or agents for early release of probes from endosomes such as pH sensitive polymeric materials or ligands selected from certain viruses. In certain other preferred embodiments, the probe may be delivered using a transfection agent, which may be lipid-, polymer-, dendrimer-based or their combinations, or their combinations with themselves or with other ligands such as peptides, proteins, and small molecules.

4. Pharmaceutical Compositions

Pharmaceutical unit dosage forms of the disclosed nanoparticles of this disclosure are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure will typically vary depending on their use. A parenteral dosage form may contain more or less of the disclosed nanoparticles than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Pharmaceutical compositions and unit dosage forms of the disclosed nanoparticles typically also include one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that include primary or secondary amines are particularly susceptible to such accelerated decomposition.

The disclosure further encompasses pharmaceutical compositions and dosage forms that include one or more compounds that reduce the rate by which the nanoparticle compositions will decompose. Such compounds, which are referred to herein as "stabilizers," include, but are not limited to, antioxidants such as ascorbic acid, pH buffers, or salt buffers. In addition, pharmaceutical compositions or dosage forms of the nanoparticle compositions may contain one or more solubility modulators, such as sodium chloride, sodium sulfate, sodium or potassium phosphate or organic acids. A specific solubility modulator is tartaric acid.

Like the amounts and types of excipients, the amounts and specific type of nanoparticles in a dosage form may differ depending on factors such as, but not limited to, the route by which it is to be administered to patients.

Topical dosage forms of the disclosed nanoparticles include, but are not limited to, creams, lotions, ointments, gels, sprays, aerosols, solutions, emulsions, and other forms know to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semisolid or solid forms including a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18th Ed., Mack Publishing, Easton, Pa. (1990).

Transdermal and mucosal dosage forms of the compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof; to form dosage forms that are non-toxic and pharmaceutically acceptable.

Depending on the specific tissue to be treated, additional components may be used prior to, in conjunction with, or subsequent to treatment with the nanoparticles of the disclosure. For example, penetration enhancers can be used to assist in delivering the nanoparticles to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the nanoparticles. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent.

5. Kits

Still another embodiment provides a kit containing the disclosed noble metal nanoparticles, optional reagents such as buffers, stabilizers, preservatives, carriers, etc., and instructions for using the nanoparticles for the detection or treatment of a pathology. The kit can optionally contain reagents for coupling a binding moiety to the nanoparticles, protocols for coupling the binding moiety to the nanoparticles, and control spectra of the nanoparticles. In some aspects the kit contains nanoparticles coupled to binding moieties. In still other aspects, the kit contains a plurality of binding moieties that can be coupled to the nanoparticles.

Materials and Methods

Preparation of Anti-EGFR Antibody Conjugated Gold Nanoparticles

Au nanoparticles were prepared by the citrate reduction of $HAuCl_4$. The measured absorption maximum of the nanoparticles was 530 nm, TEM showed the average particle size of 35 to 40 nm. The anti-EGFR/gold conjugates were prepared according to the method described by Sokolov et al. *Technology in Cancer Research & Treatment* 2003, 2(6), 491-504. Briefly, the gold NPs were diluted in 20 mM HEPES buffer (pH 7.4, Sigma) to a final concentration with optical density of 0.8 at 530 nm. 50 µL anti-EGFR monoclonal antibodies (host mouse; Sigma) were diluted in 500 µL of the same HEPES buffer. Then 10 mL of the Au solution prepared above were mixed with the dilute antibody solution for 20 mins. 0.5 mL of 11% polyethyleneglycol (MW=4000, Boehringer Mannheim) was added to the mixture to prevent aggregation, and the solution was centrifuged at 6000 rpm for 18 mins. Then, the anti-EGFR/Au pellet was dispersed in PBS buffer (pH=7.4, Cellgro) and stored at 4° C.

Nanoparticles Incubation, Laser Treatment and Light Scattering Imaging

One benign epithelial cell line, HaCaT (human keratinocytes), and two malignant-epithelial cell lines (human oral squamous cell carcinoma), HOC 313 clone 8 and HSC 3, were cultured on 18 nm u diameter glass cover slips in a 12-well tissue culture plate in DMEM plus 5% FBS at 37° C. under 5% $CO_2$. The cover slips were coated with collagen type I (Roche) in advance for optimum cell growth.

For the laser irradiation experiment the CW argon laser was chosen due to wavelength close to the absorption maxima of the nanoparticles. The cell monolayer was immersed into the conjugated nanoparticles solution (~0.2 nM) for 40 min, rinsed with PBS buffer and then exposed to argon laser light at various power densities. The argon laser at 514 nm was focused by a lens (f=10 cm) to form a round spot with 1 mm in diameter on the sample position. Multiple regions on the slides were exposed to argon laser light at different power densities for 4 min each and then stained with 0.4% trypan blue (Sigma) for 10 mins to test cell viability. Dead cells will accumulate the dye and will stain blue while live cells will pump out it and remain clear. After staining, the samples were imaged under 10× in a transmission mode.

For the light scattering imaging, the cells after laser exposure and staining were fixed with 1.6% paraformaldehyde and sealed with another cover slip with a small amount of glycerol. The light scattering images were taken using an inverted Olympus IX70 microscope in which a dark filed condenser (U-DCW) delivers a very narrow beam of white light from a Halogen lamp on top of the samples. A 100×/1.35 oil Iris objective (UPLANAPO) was used to collect only the scattered light from the samples.

Synthesis of Gold Nanorods.

The nanorods are synthesized according to the seed-mediated growth method with some modifications. Briefly, 0.0005 M auric acid in 0.2 M CTAB are reduced at room temperature by cold sodium borohydride (0.01M) to yield small nanoparticles (less than 5 nm) as a seed solution. A 100 mL growth solution is prepared by reduction of 0.001 M auric acid (with 0.004 M silver salt added before) in 0.2 M CTAB and 0.15 M BDAC with 70 µl of 0.0788 M ascorbic acid. Then 8 µl seed solution is introduced into the growth solution and the nanorods are obtained after several hours. Higher yield of nanorods will be obtained after longer time. Nanorods with various aspect ratios can be obtained by changing the silver concentrations.

Preparation of Anti-EGFR/Nanorod Conjugates.

The nanorods prepared as above are capped by a bilayer of cetyltrimethylammonium bromide (CTAB) and are negatively charged. The original rods prepared in this way are centrifuged at 14000 rpm twice to get rid of the extra CTAB in solution. Then the negatively charged surface of the nanorods is changed to positively charged by exposing the nanoparticles to poly(styrenesulfonate) (PSS, MW=18,000) polyelectrolyte solutions. The extra PSS in solution is separated by centrifuging the rod solution at 8000 rpm and then redispersed in pH=7.4 PBS buffer. The antibodies are bound to the PSS coated nanorods according to the methods of binding antibodies to nanosphere described above. The nanorods conjugated with anti-EGFR monoclonal antibodies are redispersed into PBS to form a stock solution with the longitudinal absorption maximum at 800 inn with optical density around 0.5. The anti-EGFR/nanorod conjugates are stable at 4° C. for several days.

Cell Culture and Cellular Incubation with Anti-EGFR/Nanorod.

One benign epithelial cell line, HaCaT (human keratinocytes) and two malignant epithelial cell lines (human oral squamous cell carcinoma) HOC 313 clone 8 and HSC 3 were cultured in DMEM plus 5% BBS at 37° C. under 5% $CO_2$. The cells are cleaved by trypsin and replated onto 18 mm glass cover slips in a 12-well tissue culture plate and are let to grow for 3 days. The cover slips were coated with collagen type I (Roche) in advance for optimum cell growth. The cell monolayer on the cover slips was taken out of the medium from the incubator and rinsed with PBS buffer and then immersed into the anti-EGFR conjugated nanorods solution for 30 min at room temperature. After nanorods incubation, the cell monolayer is rinsed with PBS buffer, fixed with paraformaldehyde and sealed with another cover slip with a small amount of glycerol.

Surface Plasmon Absorption and Scattering of Gold Nanorods on Cells.

The light scattering images were taken using an inverted Olympus IX70 microscope using a highly numerical dark field condenser (U-DCW, 0.9-1.2) which delivers a very narrow beam of white light from a tungsten lamp on top of the samples. A 100×/1.35 oil Iris objective (UPLANAPO) was used to collect only the scattered light from the samples. The dark field pictures were taken using an Olympus film camera using Kodak E100 VS film. The absorption spectra of gold nanoparticles on single cells were measured using SEE1100 micro-spectrometer under 20× magnification with focus area of 8 μm.

NIR Photothermal Therapy.

For the laser irradiation experiment, the CW Ti:Sapphire laser at 800 nm is used due to its overlapping with the absorption maximum of the nanorods, which is where the tissues have least absorption. The cell monolayer was immersed into the conjugated nanoparticles solution ($OD_{800nm}$=0.5) for 30 min, rinsed with PBS buffer and then exposed to the red laser light at various power densities. The red laser at 800 nm was focused by a lens to form a round spot with 1 mm in diameter on the sample position. Multiple regions on the slides were exposed to the laser light at different power densities for 4 min each and then stained with 0.4% trypan blue (Sigma) for 10 mins to test cell viability. Dead cells will accumulate the dye and stain blue while live cells will pump out it and remain clear. After staining, the samples were imaged under 10× in bright field.

The following examples are included to demonstrate preferred embodiments of the disclosed subject matter. The examples are merely illustrative and not exhaustive of the applications of the disclosure. It should be appreciated by those of skill in the art that the techniques disclosed in the examples which follow, represent techniques which function well in the practice of the various embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Antibody Conjugated Nanospheres can be Used to Distinguish Between Malignant and Non-Malignant Cells A very simple and inexpensive conventional microscope with proper rearrangement of the illumination system and the light collection system was used to imaging cells which were incubated with colloidal gold or with anti-epidermal growth factor receptor (anti-EGFR) antibody conjugated gold nanoparticles. The optical properties of the gold nanoparticles incubated in single living cancerous and noncancerous cells are compared for different incubation methods. It is found that the scattering images and the absorption spectra recorded from anti-EGFR antibody conjugated gold nanospheres incubated with cancerous and noncancerous cells are very different and offer potential techniques for cancer diagnostics.

One nonmalignant epithelial cell line HaCaT (human keratinocytes), and two malignant epithelial cell lines HOC 313 clone 8 and HSC 3 (human oral squamous cell carcinoma) were cultured on 18 mm diameter glass cover slips in a 12-well tissue culture plate in DMEM plus 5% FBS at 37° C. under 5% $CO_2$. The cover slips were coated with collagen type I (Roche) in advance for optimum cell growth. For the incubation of colloidal gold, nanoparticles (~0.3 nM) were added into the medium and the cells were grown for 48 hours. The cells on the cover slips were then rinsed with PBS buffer and fixed with 1.6% paraformaldehyde and sealed with another cover slip with a small amount of glycerol. For the incubation of conjugated nanospheres, the cells were grown on the cover slips for 48 hours and then the cell monolayer was immersed into the conjugated nanoparticles solution for 40 min, then rinsed with PBS buffer, fixed with paraformaldehyde and sealed as above.

The light scattering images were taken using an inverted Olympus IX70 microscope in which the illumination system is removed and replaced by an illumination condenser (U-DCW) which delivers a very narrow beam of white light from a mercury lamp on top of the samples. A 100×/1.35 oil Iris Ph3 objective (UPLANAPO) with adjustable phase contrast ability was used to collect only the scattered light from the samples. When the phase contrast and the focus are optimized, the center illumination light beam doesn't enter the light collection cone of the microscope objective and only the scattered light of the side beam by the sample is collected. This presents an image of bright object in a dark background. The absorption spectra of gold nanoparticles inside a single cell were measured using SEE1100 micro-spectrometer under 20× magnification.

Gold nanospheres with the average sizes of 35 nm were chosen after experimental determination of the particle uptake efficiency, the cellular labeling efficiency and the light scattering intensities of the nanoparticles. Gold nanoparticles are introduced into cells by the endocytosis process during cell differentiation and proliferation processes. Smaller nanoparticles cross the cytoplasmic membrane more easily but their scattering light crossection is smaller than larger nanoparticles. They also give more greenish scattered color which cannot be easily resolved from the scattered green light from the cellular organelles. Larger nanoparticles have higher scattering crossection but have smaller labeling efficiency possibly due to steric hindrance. For this experiment, 15 nm and 60 nm nanoparticles were also used, but neither one is found to be more efficient than the 35 nm nanoparticles in either the amount of colloid nanoparticles uptake into cells or the labeling efficiency for cancer cells detection when anti-EGFR antibodies are used.

FIG. 1 shows the light scattering images of the HaCaT noncancerous cells (left column), HOC cancerous cells (middle column) and HSC cancerous cells (right column) without nanoparticles. All the cells show dim greenish light (two images were shown for each type of cells for comparison). This green light is due to autofluorescence and scattered light from the cell organelles in cell cytoplasm and membrane. From this figure show that the three types of cells have different structure characteristics. HOC cancer cells are almost 4 times larger than HaCaT or HSC cells. HaCaT and HSC cells show almost homogenous diamond shapes while HOC cells have other shapes for some cells.

When incubated in the presence of nanospheres, the cells grow at a normal rate and the nanospheres are accumulated inside the cells. The incorporated gold nanospheres scatter strong yellowish light and make individual cells easily identifiable. Three images for each kind of cell are shown to test reproducibility (FIG. 2). Examination reveals that gold nanospheres are predominantly accumulated inside the cytoplasm of the cells. In most HaCaT noncancerous cells (left column) the gold nanospheres demonstrate a spotted pattern inside the cytoplasm while the nanospheres are homogenously distributed in the cytoplasm of HOC (middle column) and HSC (right column) cancerous cells. The difference of the distribution of nanospheres inside cells may reflect the difference of the cell differentiation and proliferation processes. The HSC specimens give the strongest scattering light due to the large amount of accumulated gold nanoparticles.

Using micro-UV-Visible spectroscopy, the absorption spectra of gold nanospheres from single cells are obtained shown in the bottom row of FIG. 2. To statistically characterize the surface plasmon absorption of the gold nanospheres inside the cells, 25 cells of each kind are measured. The nanospheres inside all cells have a major peak around 545 nm characteristic of the surface plasmon absorption of the individual nanoparticles inside the cytoplasm of the cells which are red shifted by 16 nm compared to the colloid nanoparticles suspension at 529 nm. This suggests that the nanoparticle surface has a different dielectric environment when present inside the cells. The broad absorption around 700 nm of the gold nanoparticles inside the cells is characteristic of the aggregated gold nanospheres. Aggregation of the nanospheres is likely induced by the salts in both the growth medium and the cytoplasm of the cells. The capping material could also be dissolved inside cells and thus leads to aggregation of the resulting metallic nanostructures. In HSC cells, the aggregates have the absorption maximum around 715 nm. In HaCaT cells, the size of these large aggregates is smaller as concluded from the shorter wavelength surface plasmon absorption maximum. The absorption of the aggregates inside HOC is not as resolved due to the shorter wavelength (679 nm) which is close to the absorption maximum of the surface plasmon absorption of the individual nanoparticles. The different sizes of the aggregates inside different kind of cells may reflect the difference in the cell cytoplasm medium or differences in the intracellular processing of the nanoparticles by the cells. The ability to resolve aggregates within cells by SPRA spectroscopy suggests that different capping agents could be utilized to monitor intracellular processes as aggregates are formed.

Example 2

Light Scattering Images of Antibody Conjugated Nanospheres

Figure 3A:
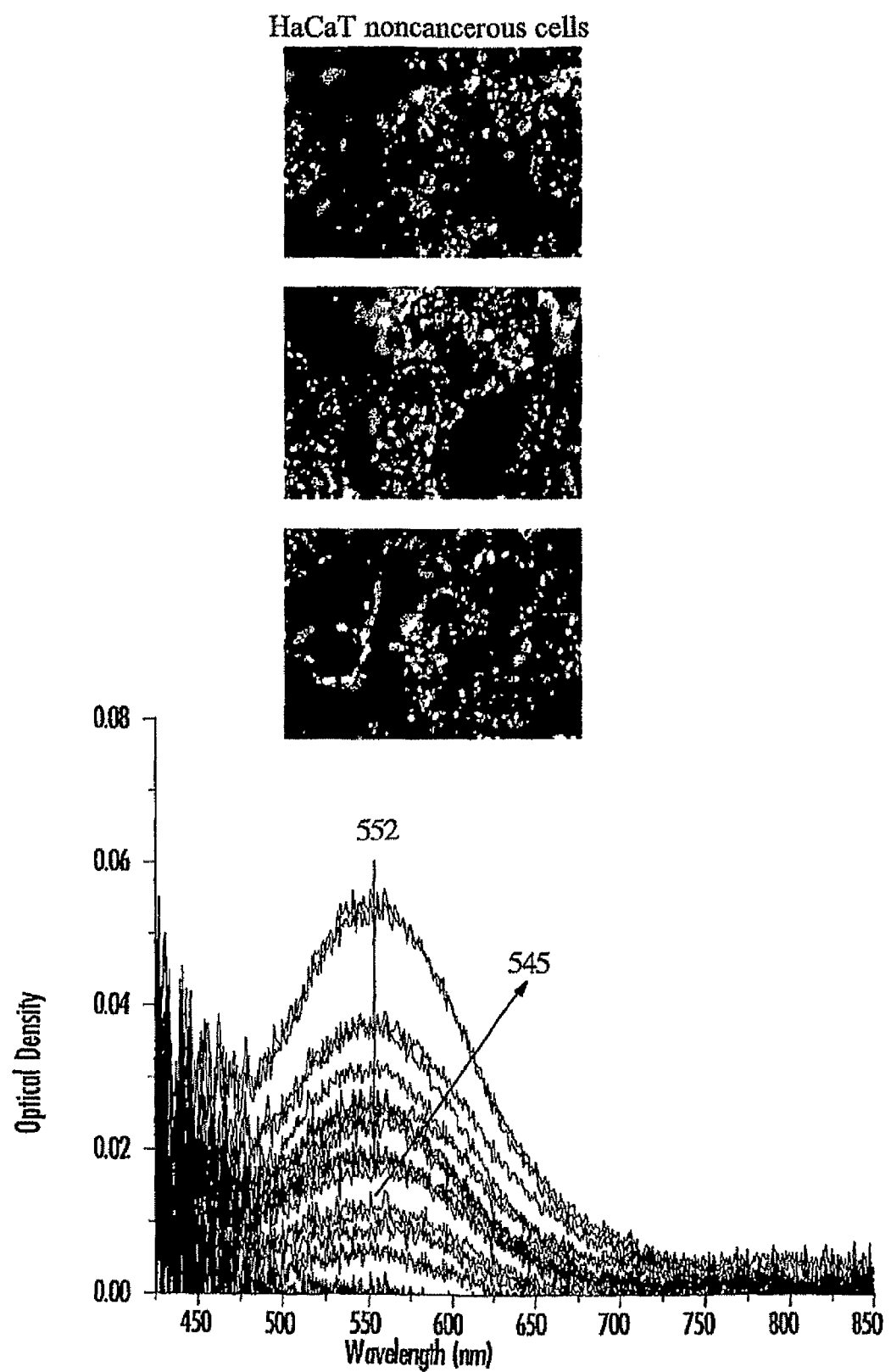
FIG. 3 shows light scattering dark field images and micro-absorption spectra of HaCaT noncancerous cells (left column), HOC cancerous cells (middle column) and HSC cancerous cells (right column) after incubation with anti-EGFR antibody conjugated gold nanoparticles. Scale bar: 10 μm for all images.
Figure 3B:
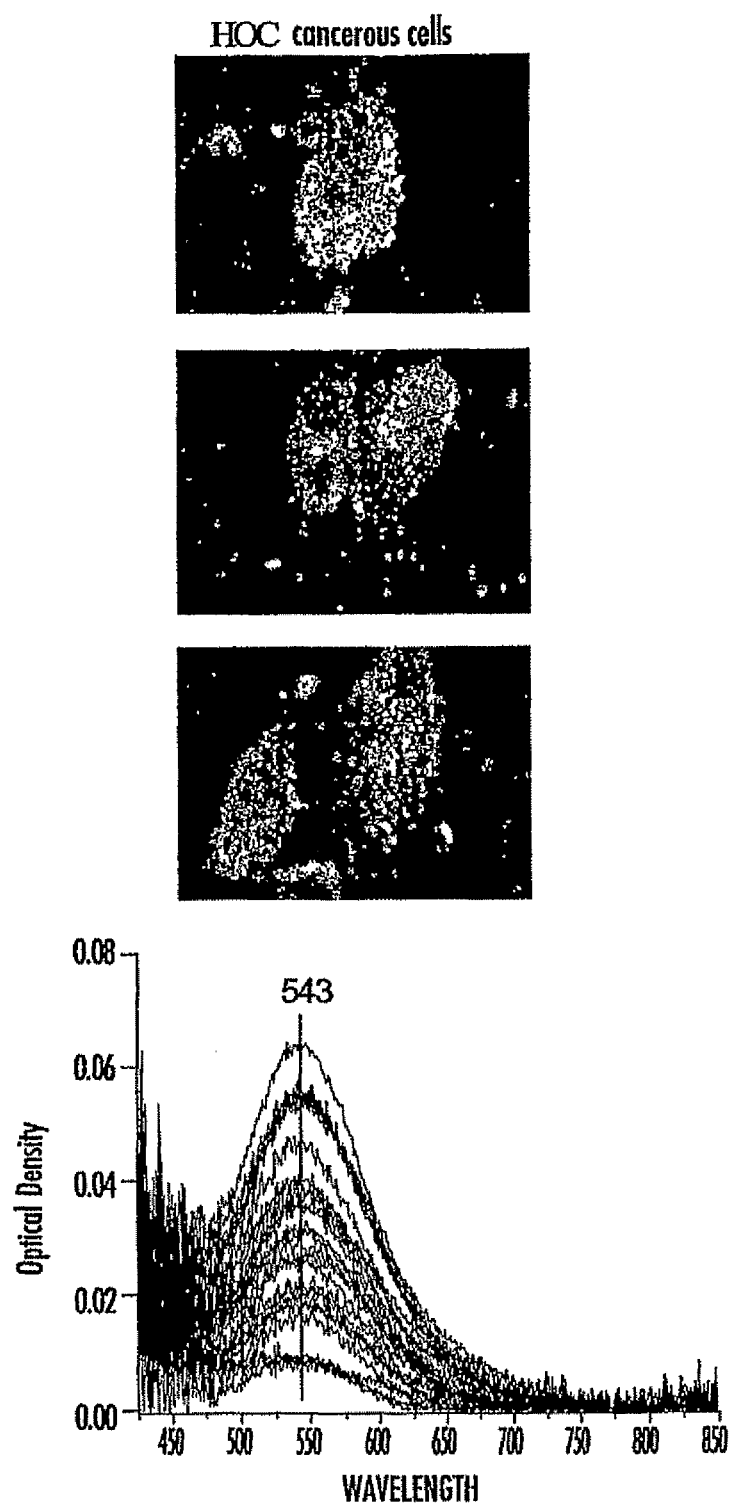
Figure 3C:
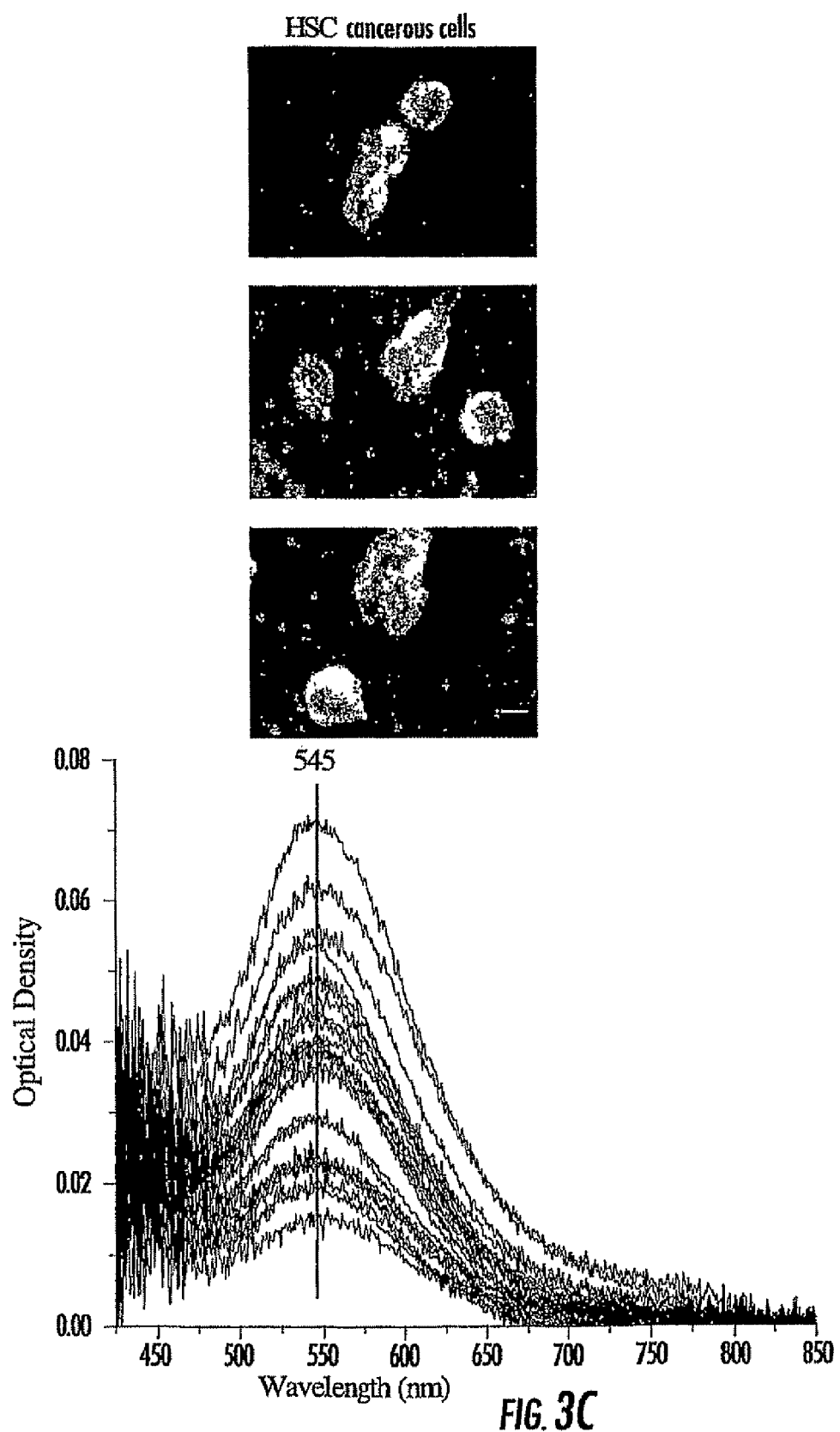

The light scattering pattern of gold nanoparticles is significantly different when anti-EGFR antibodies were conjugated to gold nanoparticles before incubation with the cells (FIG. 3). The HaCaT on cancerous cells are poorly labeled by the nanoparticles and the cells could not be identified individually (FIG. 3, three images on the left column). When the conjugates are incubated with HOC FIG. 3, three images on the middle column) and HSC (FIG. 3, tree images on the right column) cancerous cells for the same amount of time, the nanoparticles are found on the surface of the cells, especially on the cytoplasm membranes for HSC cancer cells. This contrast difference is due to the specific binding of overexpressed EGFR on the cancer cells with the anti-EGFR antibodies on the gold surface. The nanoparticles are also found on the HaCaT noncancerous cells due to part of the specific binding, but mostly due to the nonspecific interactions between the antibodies and the proteins on the cell surface and thus the nanoparticles are randomly distributed on the whole cells. The nonspecific interaction between the anti-EGFR antibodies and the collagen matrix also exists which is shown as the reddish scattering light of the gold nanoparticles on the collagen background.

When anti-EGFR antibodies are attached to the gold nanoparticles, all the absorption spectra on different cells become narrower and similar for each cell type. No absorption bands due to aggregation are observed. The nanoparticles bound to HOC and HSC cancer cells have similar absorption maxima at around 545 nm which is 9 nm red shifted compared to the isolated anti-EGFR/Au solutions at 536 nm. This red shift is due to the specific binding of the anti-EGFR antibodies on the gold surface to EGFR on the cell surface. It also could be due to the interparticle interaction resulting from the conjugates arrangement on the cell surface in two dimensions. Such spectroscopic binding undoubtedly changes the dielectric constant around the surface of the gold nanoparticles. One can use the maximum at 545 nm to characterize the conjugated nanoparticles binding to the EGFR on the cell surface. For HaCaT noncancerous cells, the particles with maximum at 545 nm are found to have a maximum absorption of 0.01 (FIG. 3) for the 25 cells measured. The rest of the nanoparticles have their maximum at 552 nm. This red shift indicates that these nanoparticles are nonspecifically bound. The maximum absorbance of the conjugated particles to cancer cells is of 0.06 for HOC cells and 0.07 for HSC cells. One can conclude that the binding ability of the anti-EGFR antibody conjugated nanoparticles to HOC and HSC cancerous cells is 600% and 700%, respectively, over the HaCaT noncancerous cells. This is undoubtedly due to the difference of the EGFR concentration on the surface of the cancer and noncancerous cells. Current optical staining techniques do not have the ability to quantify non-specific binding in this manner. The results correlate well with previously published studies which qualitatively report that most cancerous cells accumulate significantly higher amount of EGFR during the carcinoma process.

In summary, cellular imaging with improved contrast due to the strong resonant light scattering of gold nanoparticles incubated inside or on the surface of cells is obtained using a very simple and inexpensive student microscope with proper rearrangement of the illumination system and the light collection system. The nonconjugated gold nanoparticles are accumulated inside cells and aggregation takes place (FIG. 2). The observed difference in the scattering of different types of cells in this figure is mostly due to the difference in the size of the cells (FIG. 1) and not to the specific interaction of the nanoparticles with different cells. However, there is a distinct difference in the distribution of anti-epidermal growth factor receptor antibody conjugated nanoparticles when incubated with cancerous and noncancerous cells (FIG. 3).

Example 3

Selectivity of Anti-EGFR Antibody Conjugated Au Nanoparticles

Figure 4:
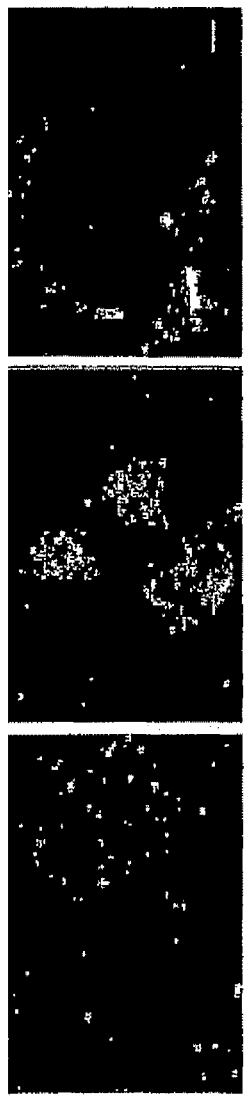
FIG. 4 shows light scattering images of HaCaT benign cells (left), HSC malignant cells (middle) and HOC malignant cells (fight) after incubation with anti-EGFR antibody conjugated gold nanoparticles used in the laser irradiation experiments. Scale bar: 10 μm

The strongly scattered colored light of gold nanoparticles is easily observed in a simple dark field setup. In live cell cultures, immuno-targeted nanoparticles successfully label and distinguish the malignant HOC and HSC cells from the HaCaT benign cells. The surface plasmon absorption spectrum itself can differentiate between the malignant and benign cells. FIG. 4 shows the light scattering pattern of anti-EGFR antibody conjugated gold nanoparticles on the surface of benign and malignant cells that are used in the laser irradiation experiment. The HaCaT cells (FIG. 4, left) are poorly labeled with the nanoparticles. When the Au conjugates are incubated with USC (FIG. 4, middle) and HOC (FIG. 4, right) for an equal amount of time, the cell surfaces are heavily labeled with the gold nanoparticles due to the specific binding of the anti-EGFR antibodies to the overexpressed EGFR on the surface of the carcinoma cells. The nonspecific interaction between the anti-EGFR antibodies and the collagen matrix seems to allow some of the nanoparticles aggregates that give the red scattering light on the collagen background.

Example 4

Laser Irradiation of Cells in Absence of Nanoparticles

Figure 5:
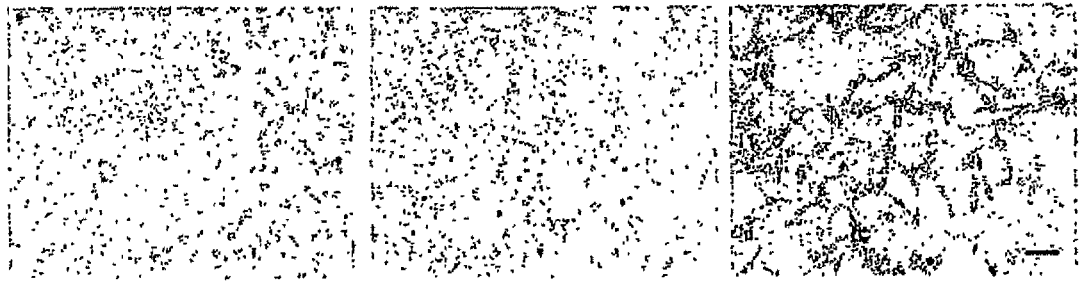
FIG. 5 shows HaCaT benign cells (left), HSC malignant cells (middle) and HOC malignant cells (right) without nanoparticles treatment irradiated at 76 W/cm$^2$ and then stained with trypan blue. No cells were killed at this laser power. Scale bar: 60 μm for all images.

Cells incubated in the absence of nanoparticles have been exposed to laser light at several power densities to test the photothermal stability of the cell themselves as controls. Laser power density of 76 W/cm$^2$, 64 W/cm$^2$, 50 W/cm$^2$, 38 W/cm$^2$, 25 W/cm$^2$ and 19 W/cm$^2$ were used to irradiate cells at different region—for 4 mins each and then stained with trypan blue. After staining, no blue cells were observed for all of the area exposed to laser irradiation. FIG. 5 shows the pictures of the cells irradiated at 76 W/cm$^2$. Even at high laser energies, no death was observed for both malignant and benign cells.

Example 5

Figure 6:
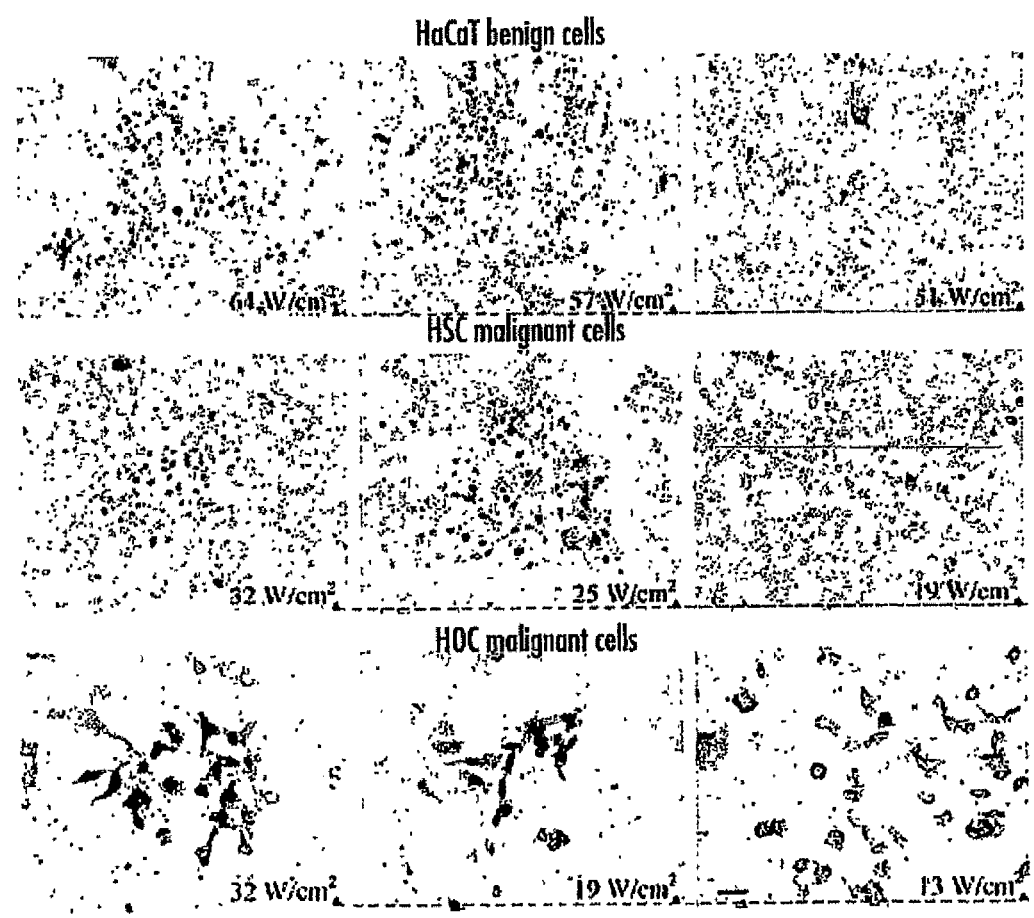
FIG. 6 shows HaCaT benign cells (top row), HSC malignant cells (middle row) and HOC malignant cells (bottom row) irradiated at different laser powers and then stained with trypan blue. HaCaT benign cells were killed at and above 57 W/cm$^2$, HSC malignant cells were killed at and above 25 W/cm$^2$ and HOC malignant cells were killed at and above 19 W/cm$^2$. Scale bar: 60 μm for all images. This shows that the cancer cells decorated with the antibody-conjugated spherical nanoparticles are killed with resonant light having intensity which is less than 50% that is needed to kill the healthy cells. This is the basis cancer treatment on the skin or within 3-5 mm under the skin.

The Laser Irradiation of Benign and Malignant Cells Incubated with Anti-EGFR/Au Conjugates After incubation with anti-EGFR antibody conjugated gold nanoparticles, cells were exposed to laser power density of 64, 57, 51, 45, 38, 32, 25, 19 and 13 W/cm$^2$ at different regions for 4 mins each to test their photothermal stability. After exposure to the argon laser at and above 57 W/cm$^2$, all HaCat cells within the laser spots became blue while at lower energy values only a few or no blue cells were detected. The top row of FIG. 6 shows the images taken at 64, 57 and 51 W/cm$^2$. HaCaT cells after incubation with anti-EGFR antibody conjugated gold nanoparticles suffered photothermal destruction when the laser has density at or higher than 57 W/cm$^2$. This is due to the introduction of the Au nanoparticles which binds to EGFR on the cell surface. The Au nanoparticles served as a photo-absorbers due to the overlapping of its absorption band ($\lambda_{max}$=530 nm) and the argon ion laser wavelength at 514 nm. The malignant HSC cells suffered irreversible photothermal injury at a much lower power density. Cell death occurred within the laser spots after exposure to laser at and above 25 w/cm$^2$ while no cell death were observed at lower power density than 19 W/cm$^2$. The middle row in FIG. 6 shows the images taken at 32, 25 and 19 W/cm$^2$. The energy threshold to cause death of the USC cells is half that which caused the photothermal death of the benign HaCaT cells.

The HOC malignant cells also undergo photothermal destruction at a much lower power density than that required for HaCaT benign cells. Cell death within the laser spots was observed at the laser power of 19 W/cm$^2$ and no cell death were observed at lower power density than 13 W/cm$^2$. The bottom row in FIG. 6 shows the images taken at 32, 19 and 13 W/cm$^2$. The transmission images reveal that more Au nanoparticles are bound to the surface of the HOC cell surface allowing for the lower energy required to cause cell death than HSC cells.

It is well known that many solid tumor cells overexpress EGFR on the cell cytoplasm membrane. Targeting a specific molecule on the cell surface allows selective delivery of the nanoparticles, and thus the photothermal energy, to the carcinoma cells (HSC and HOC), as confirmed by the results in FIG. 1. Thus it explains why lower laser energy is sufficient to produce photothermal destruction of the malignant cells, leaving the benign cells intact.

Au nanoparticles are a class of photothermal agents causing cell injury and death through conversion of the strongly absorbed light to thermal energy. Au nanoparticles are easily bioconjugatable and are potentially useful with a range of delivery vectors. By using surface plasmon resonant light scattering imaging, it is found that much more Au nanoparticles are bound to HSC and HOC malignant cells than the HaCaT benign cells through the molecular targeting of overexpressed EGFR on the malignant cell surface. After exposure of these cells treated with anti-EGFR antibody conjugated Au nanoparticles to a visible CW argon laser at 514 nm, different laser power densities were observed to cause photothermal destruction among these three types of cells. The two malignant cells require less than half the energy needed to kill the benign cells incubated with gold nanoparticles and much less than one fourth the energy required to kill the cells in the absence of nanoparticles.

Example 6

Surface Plasmon Absorption and Light Scattering of Gold Nanorods on Cells

Figure 7:
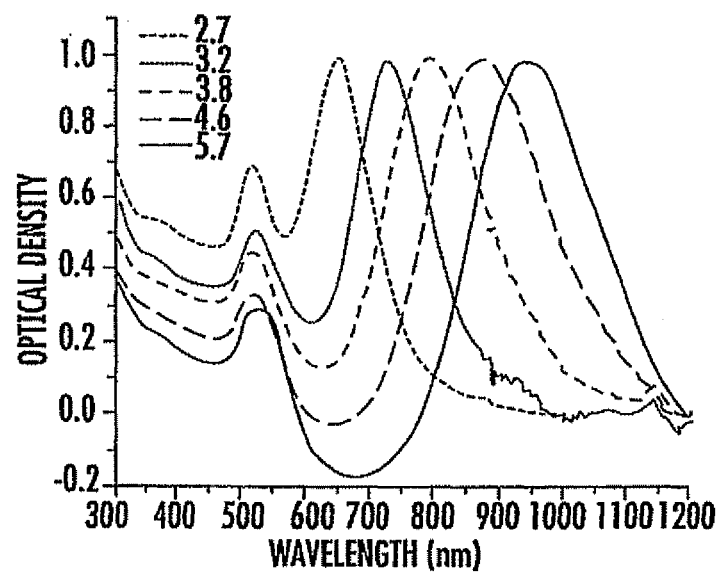
FIG. 7 shows that the absorption and scattering spectra of nanorods can be tuned to the near infrared region for in-vivo detection and therapy. (Top panel) the surface plasmon absorption spectra of nanorods at different aspect ratio showing sensitivity of the strong longitudinal band to the aspect ratio of the nanorods; Bottom: TEM image of nanorods at aspect ratio of 3.8 whose spectrum is shown on top.
Figure 7:
Figure 8A:
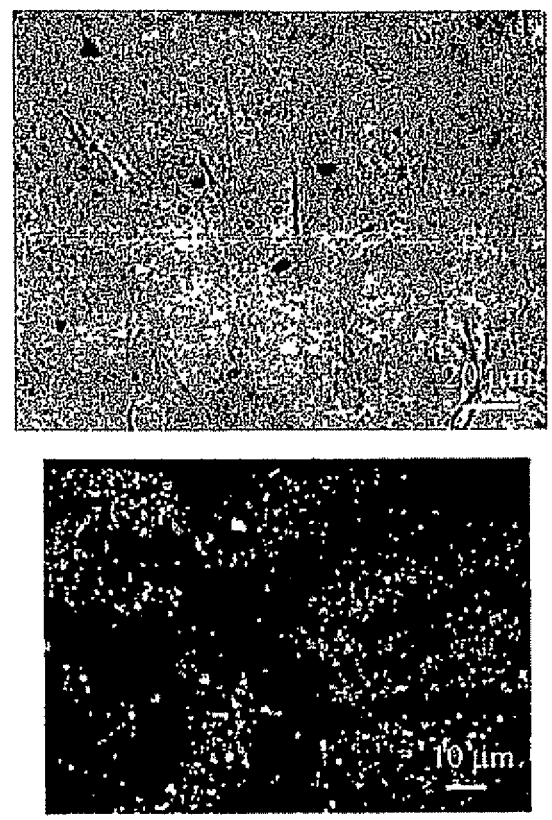
FIG. 8 shows the absorption and light scattering of anti-EGFR/Au nanorod after incubation with cells for 30 mins at room temperature. Top row: bright field images; middle row: dark field images; bottom row: the absorption spectra of nanorods from single cells (each spectrum is an average of 20 different individual cells for each kind). The dark field images show that the red light is the most enhanced corresponding to the spectral region of the surface plasmonic enhancement of the longitudinal oscillation with absorption around 800 nm.
Figure 8A:
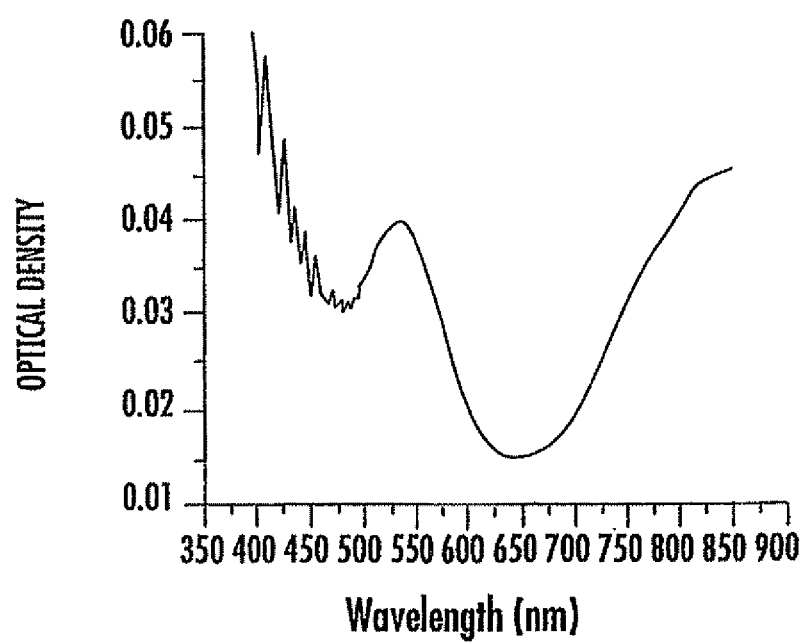
Figure 8B:
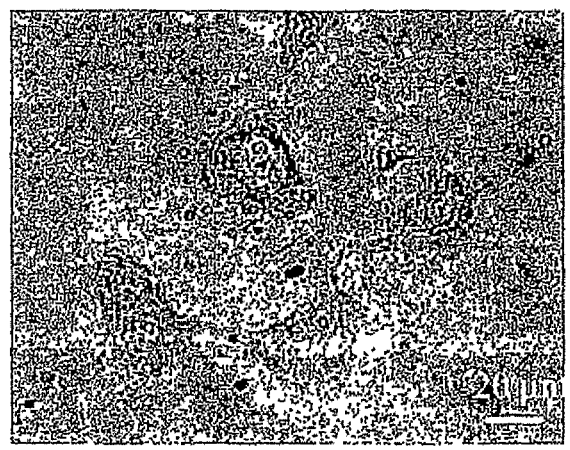
Figure 8B:
Figure 8B:
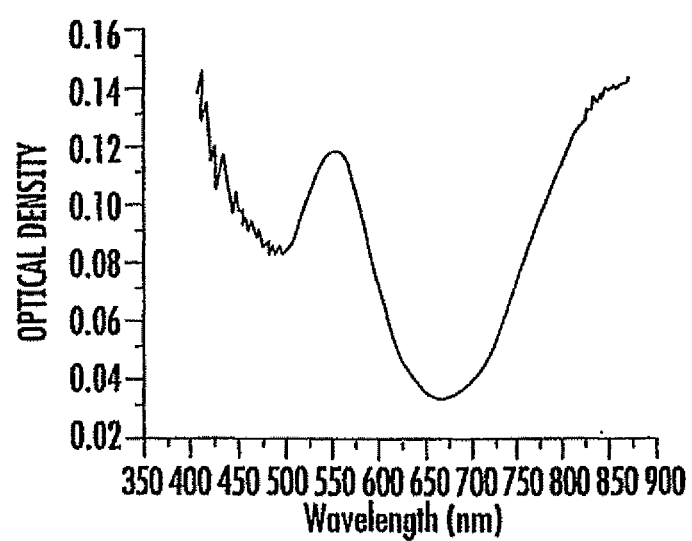
Figure 8C:
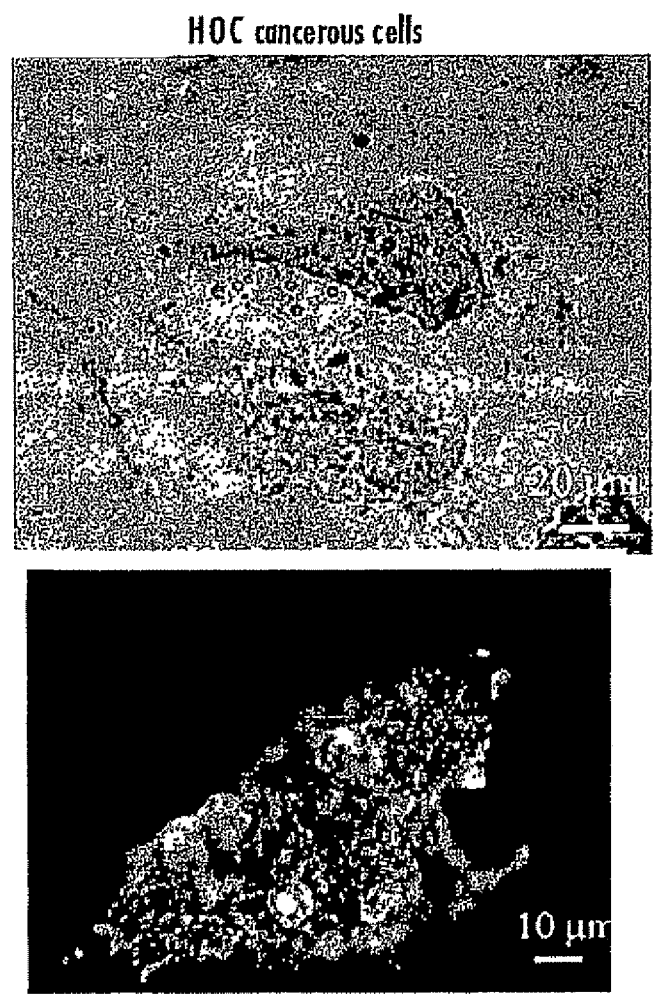
Figure 8C:
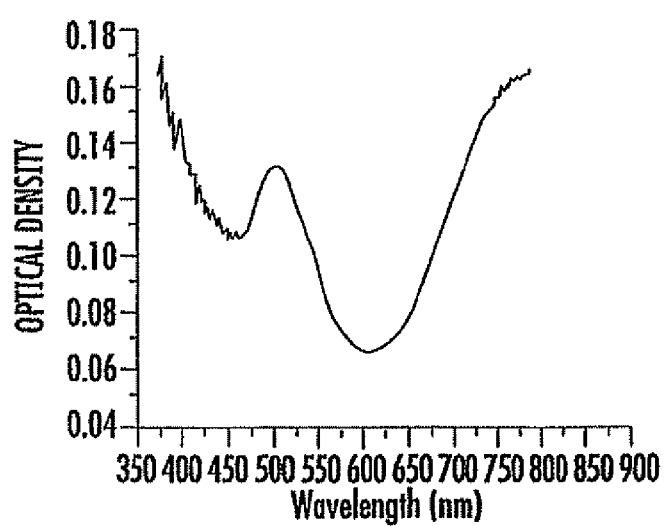

Gold nanospheres have only one visible maximal absorption band which is adjustable or tunable from about 520+/−30 nm by changing the diameter and/or adding a capping material. The surface plasmon absorption of gold nanorods has two bands: a strong longitudinal plasmon band corresponding to the light absorption along the long axis of the particle and a weak transverse plasmon band corresponding to light absorption along the short axis of the particle. FIG. 7 shows the optical absorption of gold nanorods of different aspect ratios obtained by varying the silver nitrate concentration during the growth process described above. The longitudinal absorption band shifts from the visible to the near infrared region as the rod aspect ratio increases. The TEM image in FIG. 7 shows the nanorods with an aspect ratio of 3.8 and an optical absorption is shown as red curve in the absorption spectra in FIG. 7.

Nanorods with absorption maximum around 800 nm are chosen for this research as it overlaps the region of minimum absorption of the tissue. It also overlaps Ti:Sapphire laser wavelength at 800 nm. The nanorods bind to both cancerous and noncancerous cells after the conjugates are incubated with cells at room temperature for 30 mins. However, significantly more rods bind to the cancerous cells causing the cells to be stained purple and making them visible with bright field microscopy under 10× magnification. The top row in FIG. 8 shows the bright field images of both cancerous and noncancerous cells under 60× magnification after incubation with anti-EGFR/nanorods conjugates. The HaCat noncancerous cells are barely resolvable while the HSC and HOC cancerous cells are clearly identifiable. The gold nanorods are better defined in higher resolution using dark field under 100× magnification (the middle row in FIG. 8). The nanorods scatter a strong orange color. The two cancerous cells are much better resolved than the HaCat noncancerous cells due to the specific binding of the gold nanorod conjugated anti-EGFR antibodies to the EGFR which are overexpressed on the cytoplasmon surface of the cancerous cells. The HaCat noncancerous cells show different patterns than the two cancerous cells due to the nonspecific binding of nanorods to cellular components and the less amount of gold nanorods on the cell surface. This nonspecific binding could be due to electrostatic interactions between the antibodies and the membrane proteins. It also could be due to the hydrophobic interaction between the hydrophobic alkly chain of the CTAB and the hydrophobic amino acids within the cellular proteins on the cell surface.

To quantify the amount of nanorods on each kind of cells, the absorption spectrum from single cells is measured using a micro-absorption spectrometer with focus area of 8 μm. The bottom row in FIG. 8 shows the absorption average from 20 different individual cells for each kind. The gold amounts on the two cancerous cells are about 3 times higher that that of the noncancerous cells. This quantification is not necessarily corresponding to the EGFR amounts difference between the cancerous and noncancerous cells because the noncancerous cells might take up some nanoparticles by nonspecific adsorption. Although the whole absorption spectra of the nanorods are not shown completely due to the cut off the absorption over 850 nm, it can be seen that the longitudinal absorption position is greatly red shifted compared the rods in solution which has an absorption maximum at 800 nm shown in FIG. 7. This red shift is due to the specific binding of the anti-EGFR antibodies on the gold surface to EGFR on the cell surface. It also could be due to the interparticle interaction resulting from the conjugates arrangement on the cell surface in two dimensions.

Example 7

Photothermal Therapy Using Gold Nanorods

Gold nanospheres of 40 nm in diameter can be used as efficient and selective photothermal absorbers for cancer therapy with a visible argon ion laser. The laser wavelength at 514 nm overlaps the surface plasmon absorption of the nanoparticles which has an absorption maximum at 530 nm. By conjugation with anti-EGFR monoclonal antibodies that specifically target the molecular marker EGFR, the malignant cells can be killed with less than half the laser energy required to kill the normal cells due to the overexpression of the EGFR on the surface of cancer cells. For clinical application of treating cancer in vivo, one need to use near infrared laser light that provides maximal penetration of light through tissue due to the low scattering and absorption from intrinsic chromophores.

Since the absorption band of nanoparticles can be shifted by changing the nanoparticles shapes, photothermal therapy with near infrared lasers are possible using gold nanoparticles with different shapes. Other shapes of gold nanoparticles, such as branched, and pentagon nanoparticles, as well as large prisms have the surface plasmon absorption reaching to near infrared region. Nanorods are good candidates for this application due to the accurate control of the absorption maximum to the required wavelength by changing the aspect ratio which can be realized by simply changing the silver ion amount during the rod growth process. However, other properties such as binding affinity to the antibodies must also be considered in the future.

Figures 9A, 9B:
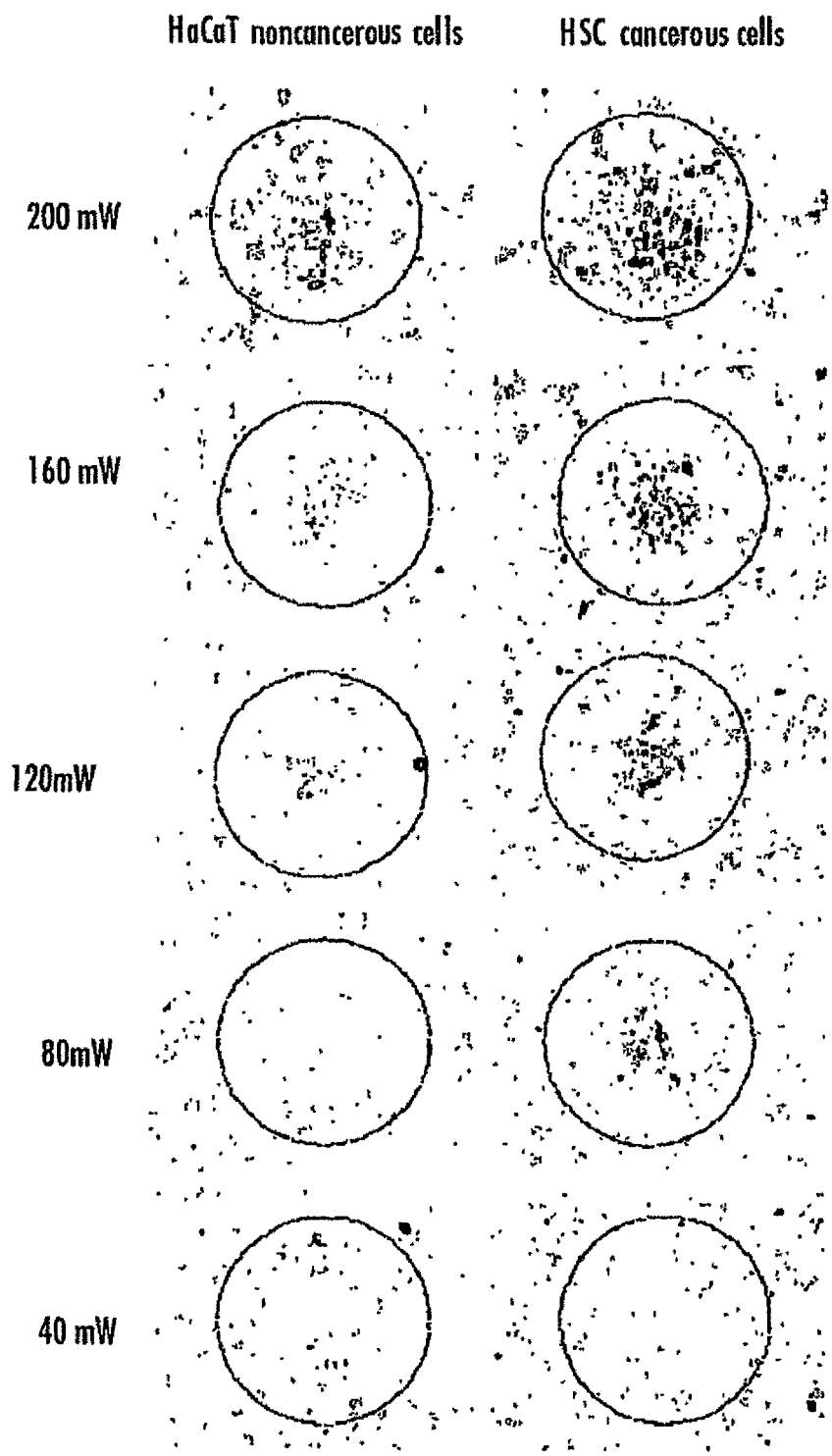
FIG. 9 shows selective photo-thermal therapy of cancer cells with anti-EGFR/Au nanorods conjugates incubated cancer cells with NIR CW at 800 nm. The circles show the laser spot on the samples. The normal HaCat cells start to be injured at 120 in W (15 W/cm$^2$) and are injured at 160 mW (18 W/cm$^2$) while the HSC and HOC cancer cells are injured at 80 mW (10 W/cm$^2$). This shows that cancer cells are killed at light with intensity which is less than 67% of the light intensity needed to kill healthy cells.
Figure 9C:
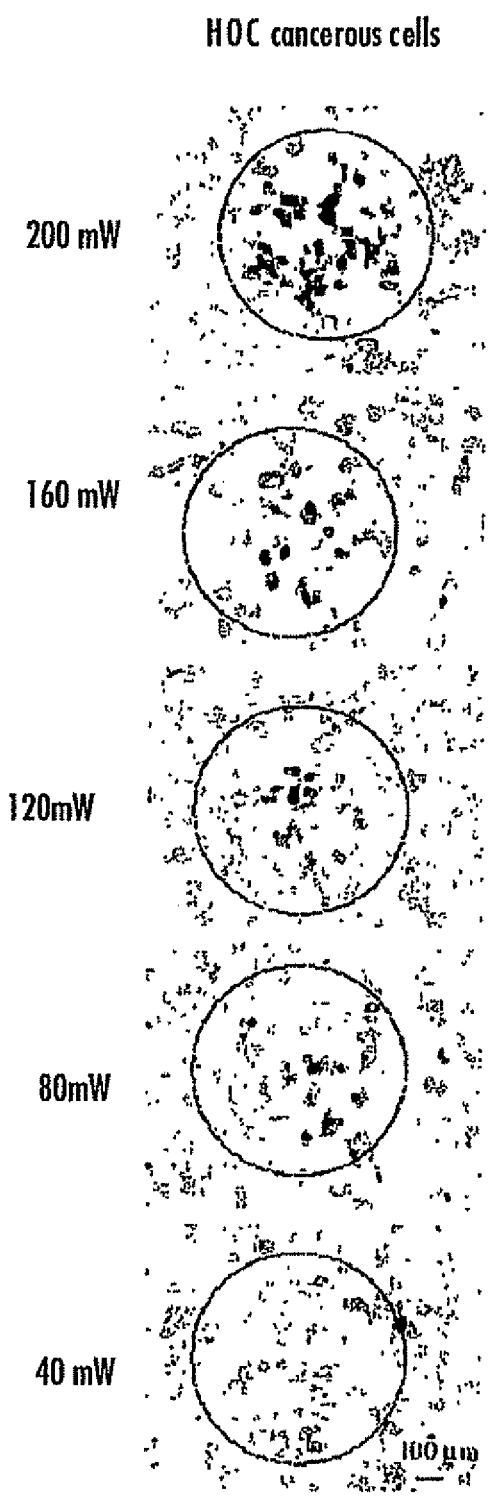

After incubation with anti-EGFR antibody conjugated gold nanorods for 30 mins, cells were exposed to laser power at 200, 160, 120, 80 and 40 mW (1 mm in diameter) for 4 mins each and then stained with trypan blue to test for their photothermal stability FIG. 9 shows images irradiated at different laser energies. After exposure to the Ti-Sapphire CW laser at 800 nm at and above 160 mW (18 W/cm$^2$), all HaCat normal cells within the laser spots underwent photothermal destruction which is shown by the cell viability test with trypan blue (FIG. 9, left column). Cell death is found in a circular region as a blue spot that matches the laser spot size. The cells outside of the laser spot are viable as indicated by their ability clear the Span blue from their cytoplasm. This also indicates that the anti-EGFR/nanorods themselves are not cytotoxic. Reducing the laser energy to 120 mW, decreases the proportion of blue cells in the laser spot. At this energy, only the laser spot center contains sufficiently high enough laser density to cause cell destruction. The energy density at the edge of the laser spot is not high enough to cause cell injury and thus the blue death cell spots become smaller than that at higher energies.

Compared to the benign HaCat cells, the malignant HSC cells suffered photothermal injury at lower 80 mW which corresponds to 9 W/cm$^2$. No cell death was observed at lower power density (FIG. 9, middle column). The energy threshold for cell death of the HSC cells is about half that needed to cause cell death of the benign HaCaT cells. The dim blue color shown on the HSC cell images outside the laser spot is due to cells that died by the long time exposure of the cells in buffer solution in air at room temperature. The HOC malignant cells also undergo photothermal destruction at and above 80 mW while no cell death was observed at lower power (FIG. 9, right column). The two malignant cells require less than half the energy needed to kill the benign cell, which is due to the overexpression of EGFR on the cancer cells. From the absorption spectra of the three types of cells in FIG. 8, it can be seen that the amount of the nanorods on the two cancer cells is about 3 times higher than that on the benign cells. This fact explains the lower laser energy required to cause cancer cell death than the noncancerous cells. These results suggest that nanorods can be used as a selective and efficient photothermal agent for cancer cell therapy using a near infrared harmless laser. Thus, for further in vivo application using near infrared laser, it is expected that the tumor tissue will be selectively destroyed at laser energies which will not harm the surrounding normal tissue due to the higher amount of nanorods target bound to the tumor tissue. Further, other forms of deliver of the nanorods could be employed, such as direct injection into the tumor. Compared to the energy used in core shell structures, laser energy used with the disclosed nanoparticles is lower. This is due to the solid gold structures which have higher energy conversion efficiency compared to the thin shell of gold in the core-shell structures due to larger absorption crossection of solid gold nanoparticles than the core-shell nanoparticles. Furthermore, the potential toxic effect of the silica core is avoided if nanorods are used.

It is known that many solid tumor including brain, bladder, stomach, breast, lung, endometrium, cervix, vulva, ovary, esophagus, stomach, prostate, renal, pancreatic, glioblastoma and in squamous cell carcinoma cells all overexpress EGFR on the cell cytoplasm membrane to different degree. Targeting this specific molecule on the cell surface allows selective delivery of the nanorods with much higher concentrations to carcinoma cells and allow for photothermal therapy with a near infrared laser for many types of cancer cells. The strong scattering of gold nanorods enables gold nanorods a class of imaging contrast agents as well. Thus, gold nanorods offer a new dual imaging/therapy method in biomedical sensing and cancer therapy.

Other methods of delivery could be utilized to deliver noble metal nanoparticles to the tumor, and other antibody markers to the cell surface could be utilized. A second unexplored target is to target the vascular endothelium of tumors by selecting markers of the tumor endothelium. Vascular endothelial growth factor receptors is one such target that could allow for destruction of a tumors blood supply. Further, nonmalignant disease can also be treated with selective photothermal therapy. Vascular growths, tumors and malformations may be targets of such a novel photothermal therapy approach such as hemangiomas, hemangioendotheliomas. Benign spindle cell tumors such as swhannomas could be targeted to reduce tumor volume and eliminate the need for dissection.

Gold nanorods are near infrared contrast agents for both molecular imaging and photothermal therapy. Solid gold nanorods have several advantages over other photothermal contrast agents. The synthesis of gold nanorods with various aspect ratios, which enable tunable absorption wavelength in the near infrared region, is readily accomplished. The sizes of the nanorods needed for the NIR application are quite small. The nanorods with 50 nm length and 15 nm in width provide absorption maximum at 800 nm. The nanorods are also facile for functionization and bioconjugation. The strong surface plasmon absorption and scattering of nanorods make them suitable or simultaneous imaging and selective therapeutic agents. In addition gold nanoparticles are generally considered nontoxic.

Gold nanorods are novel class of dual imaging/therapy contrast agents due to their strong absorption and scattering of the near infrared light. By using surface plasmon resonant light absorption spectroscopy and scattering imaging, it is found that much more gold nanoparticles are bound to HSC and HOC malignant cells than to HaCaT benign cells through the molecular targeting of overexpressed EGFR on the malignant cell surface. After exposure of these cells treated with anti-EGFR antibody conjugated Au nanoparticles to a near infrared CW Ti:Sapphire laser at 800 nm, different laser power energies were observed to cause photothermal destruction among these three types of cells. The two malignant cells are found to require less than half the energy needed to kill the benign cells incubated with gold nanorods.

What is claimed is:

1. A method for killing cancer cells in a subject in need thereof, comprising:
   a. administering to the subject one or more solid noble metal nanorods coupled to a binding moiety that specifically binds to a target substance expressed by cancer cells to a region of the subject, wherein the solid noble metal nanorods consist essentially of gold or silver metal having an aspect ratio of about 2.7 to about 10; and
   b. exposing the one or more solid noble metal nanorods to near infra-red light from a continuous wave laser at a density of at least 9 W/cm$^2$ and less than 18 W/cm$^2$; wherein the one or more solid noble metal nanorods absorbs the light and converts the absorbed light to heat, and wherein the heat kills the cancer cells.

2. The method of claim 1, wherein the region is within about 5 mm of an exterior surface of the host.

3. The method of claim 1, wherein the target substance is selected from the group consisting of epidermal growth factor receptor, transferrin receptor, platelet-derived growth factor receptor, Erb-B2, CD 19, CD20, CD45, CD52, Ep-CAM, alpha ([alpha])-fetoprotein, carcinoembryonic antigen peptide-1, caspase-8, CDC27, CDK4, carcino-embryonic antigen, calcium-activated chloride channel-2, cyclophilin B, differentiation antigen melanoma, elongation factor 2, Ephrin type-A receptor 2, 3, Fibroblast growth factor-5, fibronectin, glycoprotein 250, G antigen, N-acetylglucosaminyltransferase V, glycoprotein 100 kD, helicase antigen, human epidermal receptor-2/neurological, heat shock protein 70-2 mutated, human signet ring tumor-2, human telomerase reverse transcriptase, intestinal carboxyl esterase, interleukin 13 receptor [alpha]2 chain, [beta]-D-galactosidase 2-[alpha]-L-fucosyltransferase, melanoma antigen, melanoma antigen recognized by T cells-1/Melanoma antigen A, melanocortin 1 receptor, macrophage colony-stimulating factor, mucin 1, 2, melanoma ubiquitous mutated 1, 2, 3, New York-esophageous 1, ocular albinism type 1 protein, O-linked N-acetyl glucosamine transferase gene, protein 15, promyelocytic leukemia/retinoic acid receptor [alpha], prostate-specific antigen, prostate-specific membrane antigen, receptor-type protein-tyrosinephosphatase kappa, renal antigen, renal ubiquitous 1, 2, sarcoma antigen, squamous antigen rejecting tumor 1, 2, 3, synovial sarcoma, Survivin-2B, synaptotagmin I/synovial sarcoma, X fusion protein, translocation Ets-family leukemia/acute myeloid leukemia 1, transforming growth factor [beta] receptor 2, triosephosphate isomerase, taxol resistant associated protein 3, testin-related gene, tyrosinase related protein 1, and tyrosinase related protein 2.

4. A method for killing cancer cells in a subject in need thereof comprising:
   administering a plurality of solid gold metal nanorods consisting of gold metal having an aspect ratio of about 2.7 to about 10 and having a surface plasmon resonance absorption maximum greater than about 600 nm wherein the solid gold metal nanorods are targeted to one or more cancer cells and specifically associate with one or more cancer cells; and
   exposing the plurality of gold metal nanorods with near infra-red light at a density of at least 9 W/cm$^2$ and less than 18 W/cm$^2$ using a continuous wave laser to generate an amount of heat from the gold metal nanorods effective to kill the targeted cancer cells associated with the solid gold metal nanorods.

5. The method of claim 4, wherein the solid gold metal nanorods are targeted to cancer cells via one or more binding moieties conjugated to the solid gold metal nanorods.

6. The method of claim 4, wherein the solid gold metal nanorods are targeted to the cancer cells via a polymeric coating.

7. The method of claim 6, wherein the polymeric coating comprises polyethylene glycol.

8. The method of claim 1, wherein the near-infrared light has a wavelength of 800 nm.

9. The method of claim 4, wherein the near-infrared light has a wavelength of 800 nm.

10. The method of claim 8, wherein the nanorods are 50 nm in length and 15 nm in width.

11. The method of claim 9, wherein the nanorods are 50 nm in length and 15 nm in width.

12. The method of claim 4 wherein the amount of light effective to kill the cancer cells is about 5 to about 80% of the amount of light needed to damage non-cancerous cells.

* * * * *

```
SEQUENCE LISTING

<160> NUMBER OF SEQ ID NOS: 13

<210> SEQ ID NO 1
<211> LENGTH: 7
<212> TYPE: PRT
<213> ORGANISM: Human immunodeficiency virus

<400> SEQUENCE: 1

Lys Arg Arg Gln Arg Arg Arg
1               5

<210> SEQ ID NO 2
<211> LENGTH: 16
<212> TYPE: PRT
<213> ORGANISM: Drosophila melanogaster

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 34
<212> TYPE: PRT
<213> ORGANISM: herpes simplex virus

<400> SEQUENCE: 3

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 4
<211> LENGTH: 16
<212> TYPE: PRT
<213> ORGANISM: artificial sequence
<220> FEATURE:
<223> OTHER INFORMATION: protein transduction domain

<400> SEQUENCE: 4

Ala Ala Val Ala Leu Leu Pro Ala Val Leu Leu Ala Leu Leu Ala Pro
1               5                   10                  15

<210> SEQ ID NO 5
<211> LENGTH: 16
```

```
<212> TYPE: PRT
<213> ORGANISM: artificial sequence
<220> FEATURE:
<223> OTHER INFORMATION: protein transduction domain

<400> SEQUENCE: 5

Ala Ala Val Leu Leu Pro Val Leu Leu Pro Val Leu Leu Ala Ala Pro
1               5                   10                  15

<210> SEQ ID NO 6
<211> LENGTH: 15
<212> TYPE: PRT
<213> ORGANISM: artificial sequence
<220> FEATURE:
<223> OTHER INFORMATION: protein transduction domain

<400> SEQUENCE: 6

Val Thr Val Leu Ala Leu Gly Ala Leu Ala Gly Val Gly Val Gly
1               5                   10                  15

<210> SEQ ID NO 7
<211> LENGTH: 17
<212> TYPE: PRT
<213> ORGANISM: artificial sequence
<220> FEATURE:
<223> OTHER INFORMATION: protein transduction domain

<400> SEQUENCE: 7

Gly Ala Leu Phe Leu Gly Trp Leu Gly Ala Ala Gly Ser Thr Met Gly
1               5                   10                  15

Ala

<210> SEQ ID NO 8
<211> LENGTH: 17
<212> TYPE: PRT
<213> ORGANISM: artificial sequence
<220> FEATURE:
<223> OTHER INFORMATION: protein transduction domain

<400> SEQUENCE: 8

Met Gly Leu Gly Leu His Leu Leu Val Leu Ala Ala Ala Leu Gln Gly
1               5                   10                  15

Ala

<210> SEQ ID NO 9
<211> LENGTH: 24
<212> TYPE: PRT
<213> ORGANISM: artificial sequence
<220> FEATURE:
<223> OTHER INFORMATION: protein transduction domain

<400> SEQUENCE: 9

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 10
<211> LENGTH: 26
<212> TYPE: PRT
<213> ORGANISM: artificial sequence
<220> FEATURE:
<223> OTHER INFORMATION: protein transduction domain

<400> SEQUENCE: 10
```

-continued

```
Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 11
<211> LENGTH: 16
<212> TYPE: PRT
<213> ORGANISM: artificial sequence
<220> FEATURE:
<223> OTHER INFORMATION: protein transduction domain

<400> SEQUENCE: 11

Thr Pro Pro Lys Lys Lys Arg Lys Val Glu Asp Pro Lys Lys Lys Lys
1               5                   10                  15

<210> SEQ ID NO 12
<211> LENGTH: 7
<212> TYPE: PRT
<213> ORGANISM: artificial sequence
<220> FEATURE:
<223> OTHER INFORMATION: protein transduction domain

<400> SEQUENCE: 12

Arg Arg Arg Arg Arg Arg Arg
1               5

<210> SEQ ID NO 13
<211> LENGTH: 18
<212> TYPE: PRT
<213> ORGANISM: artificial sequence
<220> FEATURE:
<223> OTHER INFORMATION: protien transduction domain

<400> SEQUENCE: 13

Lys Leu Ala Leu Lys Leu Ala Leu Lys Ala Leu Lys Ala Ala Leu Lys
1               5                   10                  15

Leu Ala
```